(12) United States Patent
Spangler et al.

(10) Patent No.: US 7,138,121 B2
(45) Date of Patent: Nov. 21, 2006

(54) BIOSENSORS UTILIZING DENDRIMER-IMMOBILIZED LIGANDS AND THERE USE THEREOF

(76) Inventors: Brenda D. Spangler, 179 Mill Creek Rd., Livingston, MT (US) 59047; Charles W. Spangler, 179 Mill Creek Rd., Livingston, MT (US) 59047

( * ) Notice: Subject to any disclaimer, the term of this patent is extended or adjusted under 35 U.S.C. 154(b) by 0 days.

(21) Appl. No.: 10/763,413

(22) Filed: Jan. 23, 2004

(65) Prior Publication Data
US 2006/0194197 A1 Aug. 31, 2006

Related U.S. Application Data

(60) Provisional application No. 60/442,270, filed on Jan. 23, 2003.

(51) Int. Cl.
*A61K 39/40* (2006.01)
*A61K 39/395* (2006.01)
*A61K 39/38* (2006.01)
*G01N 33/566* (2006.01)
*A01N 47/00* (2006.01)
*A61K 47/32* (2006.01)

(52) U.S. Cl. .............................. 424/178.1; 424/130.1; 424/133.1; 424/141.1; 424/184.1; 436/501; 514/772; 514/772.4; 525/417

(58) Field of Classification Search ............. 424/130.1, 424/133.1, 141.1, 178.1, 184.1; 436/501; 514/772, 772.4; 525/417
See application file for complete search history.

(56) References Cited

U.S. PATENT DOCUMENTS

| | | | |
|---|---|---|---|
| 4,964,972 A | 10/1990 | Sagiv et al. |
| 5,108,573 A | 4/1992 | Rubinstein et al. |
| 5,156,810 A | 10/1992 | Ribi |
| 5,242,828 A | 9/1993 | Bergstrom et al. |
| 5,294,369 A | 3/1994 | Shigekawa et al. |
| 5,472,881 A | 12/1995 | Beebe et al. |
| 5,512,131 A | 4/1996 | Kumar et al. |
| 5,620,850 A | 4/1997 | Bamdad et al. |
| 5,776,672 A | 7/1998 | Hashimoto et al. |
| 5,834,224 A | 11/1998 | Ruger et al. |
| 5,837,832 A | 11/1998 | Chee et al. |
| 5,846,708 A | 12/1998 | Hollis et al. |
| 5,861,242 A | 1/1999 | Chee et al. |
| 5,891,630 A | 4/1999 | Eggers et al. |
| 5,942,397 A | 8/1999 | Tarlov et al. |
| 5,968,745 A | 10/1999 | Thorp et al. |
| 5,972,692 A | 10/1999 | Hashimoto et al. |
| 6,020,047 A | 2/2000 | Everhart |
| 6,066,448 A | 5/2000 | Wohlstadter et al. |
| 6,083,708 A | 7/2000 | Singh et al. |
| 6,090,545 A | 7/2000 | Wohlstadter et al. |
| 6,090,933 A | 7/2000 | Kayyem et al. |
| 6,096,273 A | 8/2000 | Kayyem et al. |
| 6,107,080 A | 8/2000 | Lennox |
| 6,127,127 A | 10/2000 | Eckhardt et al. |
| 6,140,045 A | 10/2000 | Wohlstadter et al. |
| 6,180,346 B1 | 1/2001 | Thorp et al. |
| 6,197,515 B1 | 3/2001 | Bamdad et al. |
| 6,207,369 B1 | 3/2001 | Wohlstadter et al. |
| 6,221,583 B1 | 4/2001 | Kayyem et al. |
| 6,300,141 B1 | 10/2001 | Segal et al. |
| 6,306,584 B1 | 10/2001 | Bamdad |
| 6,322,979 B1 | 11/2001 | Bamdad et al. |
| 6,361,671 B1 | 3/2002 | Mathies et al. |
| 6,472,148 B1 | 10/2002 | Bamdad et al. |
| 6,479,240 B1 | 11/2002 | Kayyem |
| 2002/0009810 A1 | 1/2002 | O'Connor et al. |
| 2002/0042074 A1 | 4/2002 | Bamdad et al. |
| 2003/0003473 A1 | 1/2003 | Kayyem et al. |
| 2003/0150723 A1 | 8/2003 | Kayyem et al. |
| 2003/0157351 A1 | 8/2003 | Swatloski et al. |

FOREIGN PATENT DOCUMENTS

| | | |
|---|---|---|
| EP | 0 339 821 A1 | 11/1989 |
| WO | WO 86/05815 A1 | 10/1986 |
| WO | WO 93/22678 A2 | 11/1993 |
| WO | WO 93/22678 A3 | 11/1993 |
| WO | WO 94/22889 A1 | 10/1994 |
| WO | WO 96/06946 A1 | 3/1996 |
| WO | WO 96/10178 A1 | 4/1996 |
| WO | WO 97/31256 A2 | 8/1997 |
| WO | WO 97/31256 A3 | 8/1997 |
| WO | WO 97/41425 A1 | 11/1997 |
| WO | WO 97/44651 A1 | 11/1997 |

(Continued)

OTHER PUBLICATIONS

Bosman, A. W., et al., "About Dendrimers: Structure, Physical Properties and Applications", Chem. Rev., 1999, 99:1665-1688.

(Continued)

*Primary Examiner*—Rodney P Swartz
(74) *Attorney, Agent, or Firm*—Robin M. Silva; Dorsey & Whitney LLP

(57) ABSTRACT

The present invention is directed to methods and compositions useful as biosensors that specifically interact with various pathogens and other target analytes. The biosensor itself, comprises functionalized dendritic tethers derivatized for attachment to a variety of surfaces as self-assembled monolayers (SAMs) as well as attached binding moieties (sometimes referred to as capture binding ligands). Accordingly, the present invention provides compositions comprising supports comprising surfaces to which the binding moieties (e.g. antibodies) are attached for the detection of target analytes (e.g. pathogens) as well as methods and compositions relating to the attachment of such binding moieties.

13 Claims, 10 Drawing Sheets

FOREIGN PATENT DOCUMENTS

| | | |
|---|---|---|
| WO | WO 98/04740 A1 | 2/1998 |
| WO | WO 98/12539 A1 | 3/1998 |
| WO | WO 98/20162 A2 | 5/1998 |
| WO | WO 98/20162 A3 | 5/1998 |
| WO | WO 98/27229 A1 | 6/1998 |
| WO | WO 98/31839 A2 | 7/1998 |
| WO | WO 98/31839 A3 | 7/1998 |
| WO | WO 98/49344 A1 | 11/1998 |
| WO | WO 98/51823 A1 | 11/1998 |
| WO | WO 98/57159 A1 | 12/1998 |
| WO | WO 99/13109 A1 | 3/1999 |
| WO | WO 99/14596 A1 | 3/1999 |
| WO | WO 99/15893 A1 | 4/1999 |
| WO | WO 99/26729 A1 | 6/1999 |
| WO | WO 99/29711 A1 | 6/1999 |
| WO | WO 01/42508 A2 | 6/2001 |
| WO | WO 01/43870 A2 | 6/2001 |

OTHER PUBLICATIONS

Chechik, V., et al., "Reactions and Reactivity in Self-Assembled Monolayers", Adv. Mater., 2000, 12(16):1161-1171.

Flink, S., et al., "Sensor Functionalities in Self-Assembled Monolayers", Adv. Mater., 2000, 12(18):1315-1328.

Hinterdorfer et al., "Surface attachment of ligands and receptors for molecular recognition force technology", Colloids and Surfaces B: Biointerfaces, 2002, 23:115-123.

Jeppesen, C., et al., "Impact of Polymer Tether Length on Multiple Ligand Receptor Bond Formation", Science, 2001, 293:465-468.

Kreppel et al., "Dynamic Glycosylation of Nuclear and Cytosolic Proteins. Cloning and Characterization of a Unique O-GlcNAc Transferase with Multiple Tetratricopeptide Repeats," J. Biol. Chem., 1997, 272(14):9308-9315.

Lahiri et al., "A Strategy for the Generation of Surfaces Presenting Ligands for Studies of Binding Based on an Active Ester as a Common Reactive Intermediate: A Surface Plasmon Resonance Study", Analytical Chemistry, 1999, 71(4):777-790.

Lubas et al., "Functional Expression of O-linked GlcNAc Transferase. Domain Structure and Substrate Specificity," J. Biol. Chem., 2000, 275(15):10983-10988.

Matthews, O.A., et al., "Dendrimers-Branching Out From Curiosities Into New Technologies", Prog. Polym. Sci., 1998, 23:1-56.

Spangler et al, "Design and Synthesis of Dendritic Tethers for the Immobilization of Antibodies for the Detection of Class A Bioterror Pathogen", Poly Preprints, 2004, 45(1):524-525.

Willemesen et al, "Simultaneous Height and Adhesion Imaging of Antibody-Antigen Interactions by Atomic Force Microscopy," Biophys. J., 1998, 75:2220-2228.

Aizawa, M., et al., "Integrated molecular systems for biosensors," Sens. Actuators B Chem. 24(1&3):1-5 (Mar. 1995).

Albers, W., et al., "Design of novel molecular wires for realizing long-distance electron transfer," Bioelectrochem. Bioenerg. 42(1):25-33 (Apr. 1997).

Bain, W., et al., "Formation of monolayers by the coadsorption of thiols on gold: variation in the length of the alkyl chain," J. Am. Chem. Soc. 111(18):7164-7175 (Aug. 1989).

Bamdad, C., "A DNA self-assembled monolayer for the specific attachment of unmodified double—or single stranded DNA," Biophys. J. 75(4):1997-2003 (Oct. 1998).

Beattie, K., et al., "Advances in genosensor research," Clin. Chem. 41(5):700-706 (1995).

Beattie, K., et al., "Genosensor Technology," Clin. Chem. 39(4):719-722 (1993).

Bilewicz, R., et al., "Monomolecular Langmuir-Blodgett films at electrodes: electrochemistry at single molecule 'gate sites'," Langmuir 11(6):2256-2266 (Jun. 1995).

Brun, A., et al., "Photochemistry of intercalated quaternary diazaaromatic salts," J. Am. Chem. Soc. 113(21):8153-8159 (Oct. 1991).

Chailapakul, O., et al., "Interactions between organized, surface-confined monolayers and liquid-phase probe molecules. 4. synthesis and characterization of nanoporous molecular assemblies: mechanism of probe penetration," Langmuir 11(4):1329-1340 (Apr. 1995).

Charych, D., et al., "Direct colorimetric detection of a receptor-ligand interation by polymerized bilayer assembly," Science 261(5121):585-588 (Jul. 1993).

Cheng, J., et al., "Selectivity and sensitivity of self-assembled thioctic acid electrodes," Anal. Chem. 64(17):1998-1999 (Sep. 1992).

Chidsey, C., et al., "Coadsorption of ferrocene-terminated and unsubstituted alkanethiols on gold: electroactive self-assembled monolayers," J. Am. Chem. Soc. 112(11):4301-4306 (May 1990).

Chiem, N., et al., "Microfluidic systems for clinical diagnostics," Transducers'97: 1997 Intl. Conf. Solid State Sens. Actuators, Chicago, IL (Jun. 16-19, 1997).

Colvin, V., et al., "Semiconductor nanocrystals covalently bound to metal surfaces with self-assembled monolayers," J. Am. Chem. Soc. 114(13):5221-5230 (Jun. 1992).

Cygan, M., et al., "Insertion, conductivity, and structures of conjugate organic oligomers in self-assembled alkanethiol monolayers on au(111)," J. Am. Chem. Soc. 120(12):2721-2732 (Apr. 1998).

Dhirani, A.A., et al., "Self-assembly of conjugated molecular rods: a high resolution STM study," J. Am. Chem. Soc. 118(13):3319-3320 (Apr. 1996).

Doktycz, M., et al., "Genosensors and Model Hybridization Studies," Automation Technologies for Genome Charaterization, T. Beugelskijk (ed.), John Wiley & Sons: New York, NY, 10:205-225 (1997).

Dong, S., "Self-assembled monolayers of thiols on gold electrodes for bioelectrochemistry and biosensors," Bioelectrochem. Bioenerg. 42(1):7-13 (1997).

Doron, A., et al., "An Electroactive photoisomerizable monolayer-electrode: a command surface for the amperometric transduction of recorded optical signals," Angew. Chem. Int. Ed. Engl. 35(13 &14):1535-1538 (Jul. 1996).

Drmanac, R., et al., "Sequencing of megabase plus DNA hybridization: Theory of the method," Genomics 4(2):114-128 (Feb. 1989).

Drobyshev, A., et al., "Sequence analysis by hybridization with oligonucleotide microchip: identification of γ-thalassemia mutations," Gene 188(1):45-52 (Mar. 1997).

Duan, C., et al., "Immbolization of proteins on gold coated porous membranes via an activated self-assembled monolayer of thiotic acid," Mikrochim. Acta. 117:195-206 (1995).

Duan, C., et al., "Separation -Free Sandwich Enzyme Immunoassays Using Microporous Gold Electrodes and Self-Assembled Monolayer/Immobilized Capture Antibodies," Anal. Chem. 66(9): 1369-1377 (May 1994).

Eggers, M., et al., "Genosensors: microfabricated devices for automated DNA sequence analysis," Adv. DNA Sequencing Tech. 1891:113-126 (1993).

Farver, O., et al., "Long-range intramolecular electron transfer in azurins," Proc. Natl. Acad. Sci. USA 86(18):6968-6972 (Sep. 1989).

Fojta, M., et al., "Supercoiled DNA-modified mercury electrode: A highly sensitive tool for the detection of DNA damage," Anal. Chim. Acta 342(1):1-12 (Apr. 1997).

Fujikawa, H., et al., "Kinetics of Escherichia coli destruction by microwave irradiation," Appl. Environ. Microbiol. 58(3):920-924 (Mar. 1992).

Gafni, Y., et al., "Biomimetic ion-binding monolayers on gold and their characterization by ac-impedance spectroscopy," Chem. Eur. J. 2(7):759-766 (1996).

Ghindilis, A, et al., "Immunosensors: electrochemical sensing and other engineering approaches," Biosens. Bioelectr. 13(1):113-131 (Jan. 1998).

Harrison D., et al., "Characterization of perifluorosulfonic acid polymer coated enzyme electrodes and a miniaturized integrated potentiostat for glucose analysis in whole blood," Anal. Chem. 60(19):2002-2007 (Oct. 1988).

Harrison, D., et al., "Immunoassay Flow Systems In-Chip," Solid-State Sens. Actuator Workshop, Hilton Head, SC (Jun. 2-6, 1996).

Hashimoto, K., et al., "DNA sensor: A novel electrochemical gene detection method using carbon electrode immobilized DNA probes," Supramol. Chem. 2:265-270 (1993).

Hochuli, E., et al., "New metal chelate adsorbent selective for proteins and peptides containing neighbouring histidine residues," *J. Chrometogr.* 411:177-184 (Dec. 1987).

Hoffmann, A., et al., "Purification of his-tagged proteins in non-denaturing conditions suggests a convenient method for protein interaction studies," *Nucleic Acids Res.* 19(22):6337-6338 (Nov. 1991).

Holmlin, R.E., et al., "Charge transfer through the DNA base stack," *Angew. Chem. Int. Ed. Engl.* 36(24):2714-2730 (Jan. 1998).

Katz, E., et al., "Application of stilbene-(4,4'-diisothiocyanate)-2,2'-disulfonic acid as a bifunctional reagent for the organization of organic materials and proteins onto electrode surfaces," *J. Electronanal. Chem.* 354(1&2):129-144 (1993).

Kelley, S. O., et al., "Electrochemistry of methylene blue bound to a DNA-modified electrode," *Bioconjug. Chem.* 8(1):31-37 (Jan.-Feb. 1997).

Kim, M., et al., "The fabrication of flow conduits in ceramic tapes and the measurement of fluid flow through these conduits," *ASME: Micro Electro Mechanical Systems-1998,* 66:171-177 (1998).

Korri-Youssoufi, H., et al., "Toward bioelectronics: specific DNA recognition based on an oligonucleotide-functionalized polypyrrole," *J. Am. Chem. Soc.* 119(31):7388-7389 (Aug. 1997).

Kunitake, M., et al., "Interfacial buffer effect of self-assembled monolayers of a carboxylic acid terminated alkanethiol of a gold electrode," *J. Chem. Soc. Chem. Commun.* 5:563-564 (1994).

Lee, G., et al., "Direct measurement of the forces between complementary strands of DNA," *Science* 266(5186):771-773 (Nov. 1994).

Lee, S.-W., et al., "A micro cell lysis device," *Sens. Actuators A* 73(1&2):74-79 (Mar. 1999).

Liu, R., et al., "Passive mixing in a three dimensional serpentine microchannel," *J. Microelectromech. Syst.* 9(2):190-196 (Jun. 2000).

McCormick, R., et al., "Microchannel electrophoretic separations for DNA in injection-molded plastic substrates," *Anal. Chem.* 69(14):2626-2630 (Jul. 1997).

McGee, D., et al., "Novel nucleosides via intramolecular functionalization of 2,2'-anhydrouridine derivatives," *Tetrahedron Lett.* 37(12):1995-1998 (Mar. 1996).

Mestel, R., "Electron Highway Points to Identity of DNA," *New Scientist* 145(1967):21 (Mar. 1995).

Michalitsch, R., et al., "Properties of self-assembled monolayers (SAMS) from thiol-functionalized oliothiophenes," *Adv. Mater.* 9(4):321-325 (Apr. 1997).

Millan, K., et al., "Voltammetric DNA biosensor for cystic fibrosis based on a modified carbon paste electrode," *Anal. Chem.* 66(18):2943-2948 (Sep. 1994).

Mir, K., et al., "Determining the influence of structure on hybridization using oligonucleotide arrays," *Nat. Biotechnol.* 17(8):788-792 (Aug. 1999).

Mirsky, V., et al., "Capacitive monitoring of protein immobilization and antigen-antibody reactions on monomolecular alkylthiol films on gold electrode," *Biosens. Bioelect.* 12(9&10):977-989 (1997).

Motesharei, K., et al., "Diffusion-limited size-selective ion ensing based on SAM-supported peptides nanotubes," *J. Am. Chem. Soc.* 119(46):11306-11312 (Nov. 1997).

Nakashima, N., et al., "An ion gate lipid monolayer membrane on gold electrodes," *J. Chem. Soc. Chem. Commun.* 4:232-233 (1991).

Napier, M., et al., "Modification of electrodes with dicarboxylate self-assembled monolayers for attachment and detection of nucleic acids," *Langmuir* 13(23):6342-6344 (Nov. 1997).

Naumann, R., et al., "Incorporation of membrane proteins in solid-supported lipid layers," *Agnew. Chem. Int. Ed. Engl.* 34(18):2056-2058 (Oct. 1995).

Nikolelis, D., et al., "Ammonium ion minisensors from self-assembled bilayer lipid membranes using gramicidin as an ionophore. Modulation of ammonium selectivity by platelet-activating factor," *Anal. Chem.* 68(10)1735-1741 (May 1996).

Niwa, M., et al., "Specific binding of concanavalin A to glycolipid monolayers on gold electrodes," *J. Chem. Soc. Chem. Commun.* 7:547-549 (1992).

Orellana, G., et al., "Photoinduced electron transfer quenching of excited Ru(II) polypyridyls bound to DNA: the role of the nucleic acid double helix," *Photochem. Photobiol.* 54(4):499-509 (Oct. 1991).

Osbourn, D., et al., "Cellulose acetate decoupler for on-column electrochemical detection in capillary electrophoresis," *Anal. Chem.* 73(24):5961-5964 (Dec. 2001).

Pang, D.-W., et al., "Modification of glassy carbon and gold electrodes with DNA," *J. Electroanal. Chem.* 403(1&2):183-188 (Feb. 1996).

Rack, J.J., et al., "Spectroscopy and electrochemistry of ruthenium-modified nucleic acids: design of a novel-metal binding nucleoside," *J. Am. Chem. Soc.* 122(26):6287-6288 (Jul. 2000).

Rojas, M., et al., "Molecular recognition at the electrode-solution interface, design, self-assembly, and interfacial binding properties of a molecular sensor," *J. Am. Chem. Soc.* 117(21):5883-5884 (May 1995).

Rüchel, R.R., "Transmission-electron microscopic observations of freeze-etched polyacrylamide gels," *J. Chromatogr. A* 166(2):563-575 (Dec. 1978).

Sabatani, E., et al., "Thioaromatic monolayers on gold: a new family of self-assembling monolayers," *Langmuir* 9(11):2974-2981 (Nov. 1993).

Sachs, S., et al., "Rates of interfacial electron transfer through conjugated spacers," *J. Am. Chem. Soc.* 119(43):10563-10564 (Oct. 1997).

Sanger, F., et al., "DNA sequencing with chain-terminating inhibitors," *Proc. Natl. Acad. Sci. USA* 74(12):5436-5467 (Dec. 1997).

Sargent, A., et al., "The electrochemistry of anitbody-modified conducting polymer electrodes," *J. Electroanal. Chem.* 470(2):144-456 (Jul. 1999).

Schlereth, D., et al., "Self-assembled monolayers with biospecific affinity for lactate dehydrogenase for the electroenzymatic oxidation of lactate," *J. Electroanal. Chem.* 431(2):285-295 (Jul. 1997).

Schuhmann, W., et al. "Electron transfer between glucose oxidase and electrodes via redox mediators bound with flexible chains to the enzyme surface," *J. Am. Chem. Soc.* 113(4):1394-1397 (Feb. 1991).

Schumm, J., et al., "Iterative divergent/convergent approach to linear conjugated oligomers by successive doubling of the molecular length: A rapid route to a 128 Å-long potential molecular wire," *Angew. Chem. Int. Ed. Engl.* 33(13):1360-1363 (Jul. 1994).

Smalley, J., et al., "Kinetics of electron transfer through ferrocene-terminated alanethiol monolayers gold," *J. Phys. Chem.* 99(35):13141-13149 (Aug. 1995).

Smith, L., et al., "Mapping and Sequencing the Human Genome: How to Proceed," *Biotechnology,* 5:933-942 (1987).

Smith, L., et al., "The synthesis and use of fluorescent aligonucleotides in DNA sequence analysis," *Meth. Enzymol.* 155:260-301(1987).

Snejdårková, M., et al., "Glucose minisensor based on self-assembled biotinylated phospholipid membrane on a solid support and its physical properties," *Bioelectrochem. Bioenerg.* 42(1):35-42 (1997).

Steinem, C., et al., "Impedance analysis of supported lipid bilayer membranes: a scrutiny of different preparation techniques," *Biochim. Biophys. Acta* 1279(2):169-180 (Mar. 1996).

Stelzle, M., et al., "On the aplication of supported bilayers as receptice layers for biosensors with electrical detection," *J. Phys. Chem.* 97(12):2974-2981 (Mar. 1993).

Storhoff, J., et al., "One-pot colorimetric differentiation of polynucleotides with single base imperfections using gold nanoparticles probes," *J. Am. Chem. Soc.* 120(9):1959-1964 (Mar. 1998).

Sun, S., et al., "Preparation of active Langmuir-Bloodgett films of glucose oxidase," *Langmuir* 7(4):727-737 (Apr. 1991).

Terrettaz, S., et al., "Protein binding to supported lipid membranes: investigation of the cholera toxin-ganglioside interaction by simultaneous impedance spectroscopy and surface plasmon resonance," *Langmuir* 9(5):1361-1369 (May 1993).

Thorp, H., et al., "Cutting out the middleman: DNA biosensors based on electrochemical oxidation," *Trends Biotechnol.* 16(3):117-121 (Mar. 1998).

Tsukahara, K., "Kinetics and mechanisms of reduction of metmyoglobins. Importance of the geometry change at the heme iron site upon reduction," *J. Am. Chem. Soc.* 111(6):2040-2044 (Mar. 1989).

Turro, N.J., et al., "Molecular recognition and chemistry in restricted reaction spaces. Photophysics and photoinduced electron transfer on the surfaces of micelles, dendrimers, and DNA," *Acc. Chem. Res.* 24(11):332-340 (Nov. 1991).

Turyan, I., et al., "Selective determination of CR(VI) by self-assembled monolayer-based electrode," *Anal. Chem.* 69(5):894-897 (Mar. 1997).

Wallace, W., et al., "Electron transfer of yeast cytochrome c immobilized on sam modified gold electrodes", *Book of Abstracts, 214th ACS National Meeting,* Las Vegas, NV, PHYS-326, American Chemical Society: Washington, DC (Sep. 7-11, 1997).

Wang, J., et al., "DNA biosensor for the detection of hydrazines," *Anal. Chem.* 68(13):2251-2254 (Jul. 1996).

Willner, I., et al., "Electrical communication between electrodes and NaD(P)+ -dependant enzymes using pyrroloquinolinequinon-enzyme electrodes in a self-assembled monolayer configuration: design of a new class of amperometric biosensors," *Anal. Chem.* 66(9):1535-1539 (May 1994).

Wood, J. C., et al., "Time-frequency transforms: a new approach to first heart sound frequency dynamics," *IEEE Transact. Biomed. Eng.* 39(7):730-740 (1992).

Zehner, R., et al., Electrochemical evaluation and enhancement via heterogeneous exchange of the passivating properties and stability of self-assembled monolayers derived from the rigid rod arenethiols, $X-C_6H_4-C=C_6H_4-C=C-C_6H_4-SH$ (X=H and F), *Langmuir* 13(11):2973-2979 (May 1997).

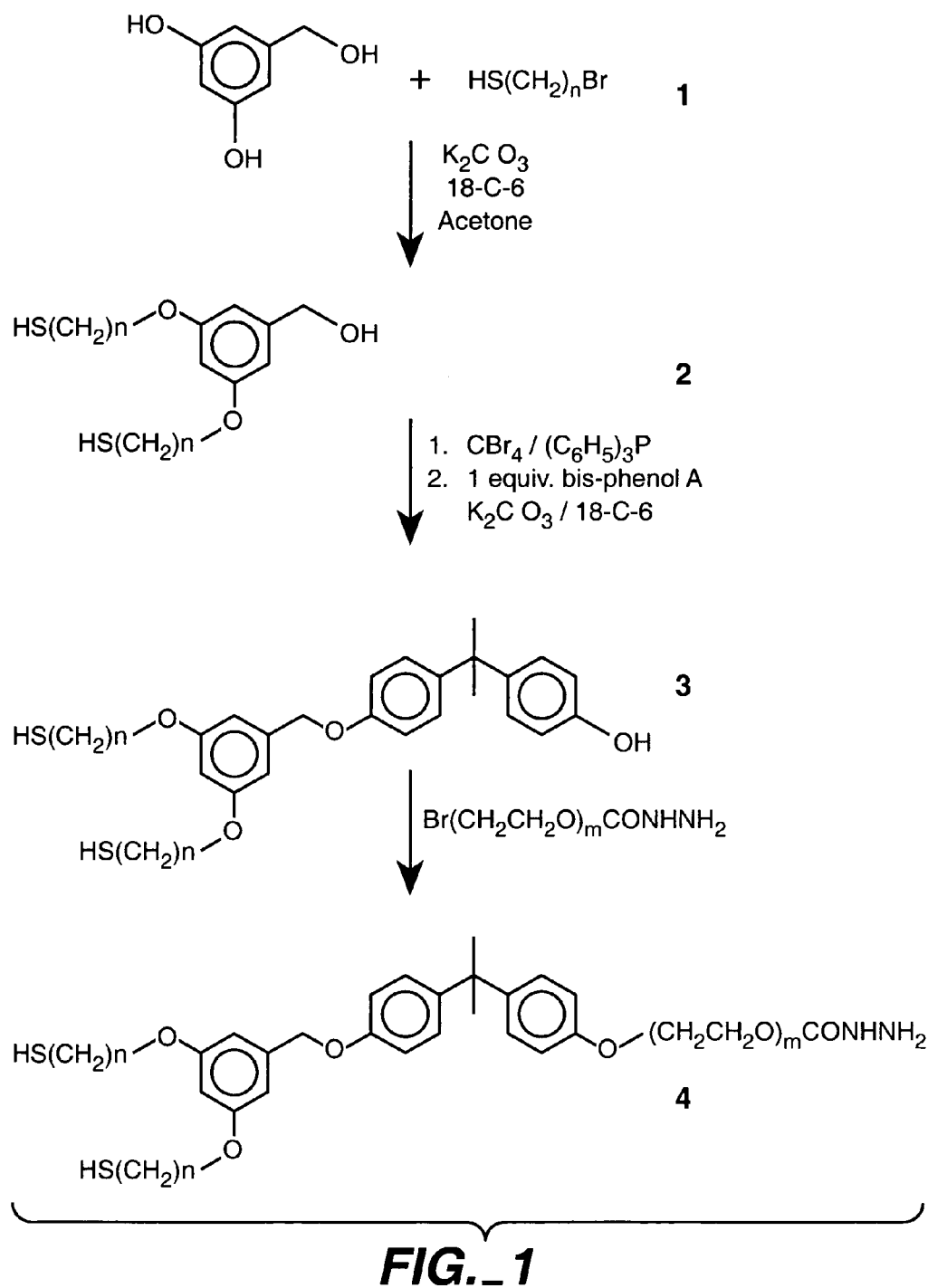
FIG._1

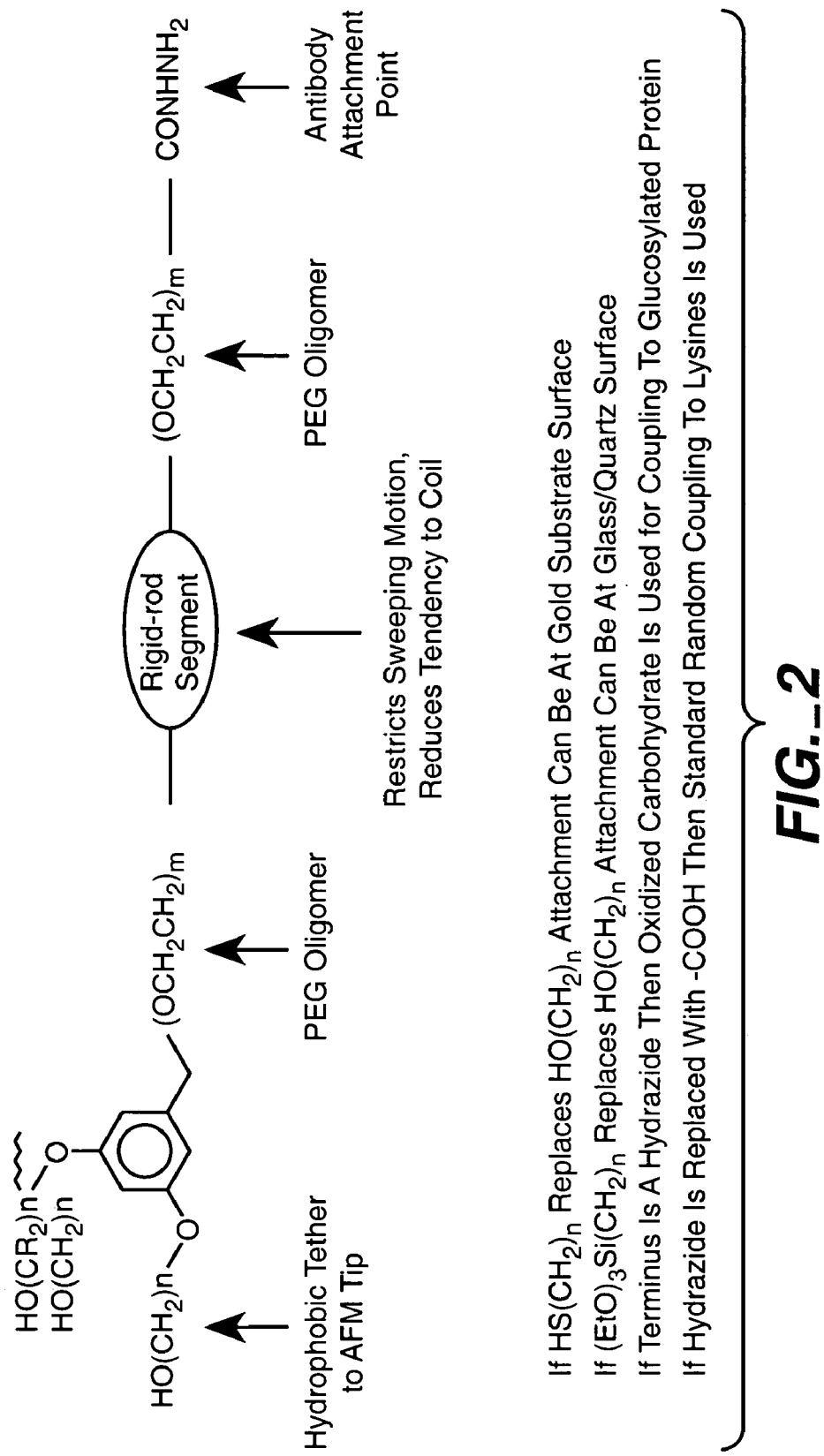
FIG._2

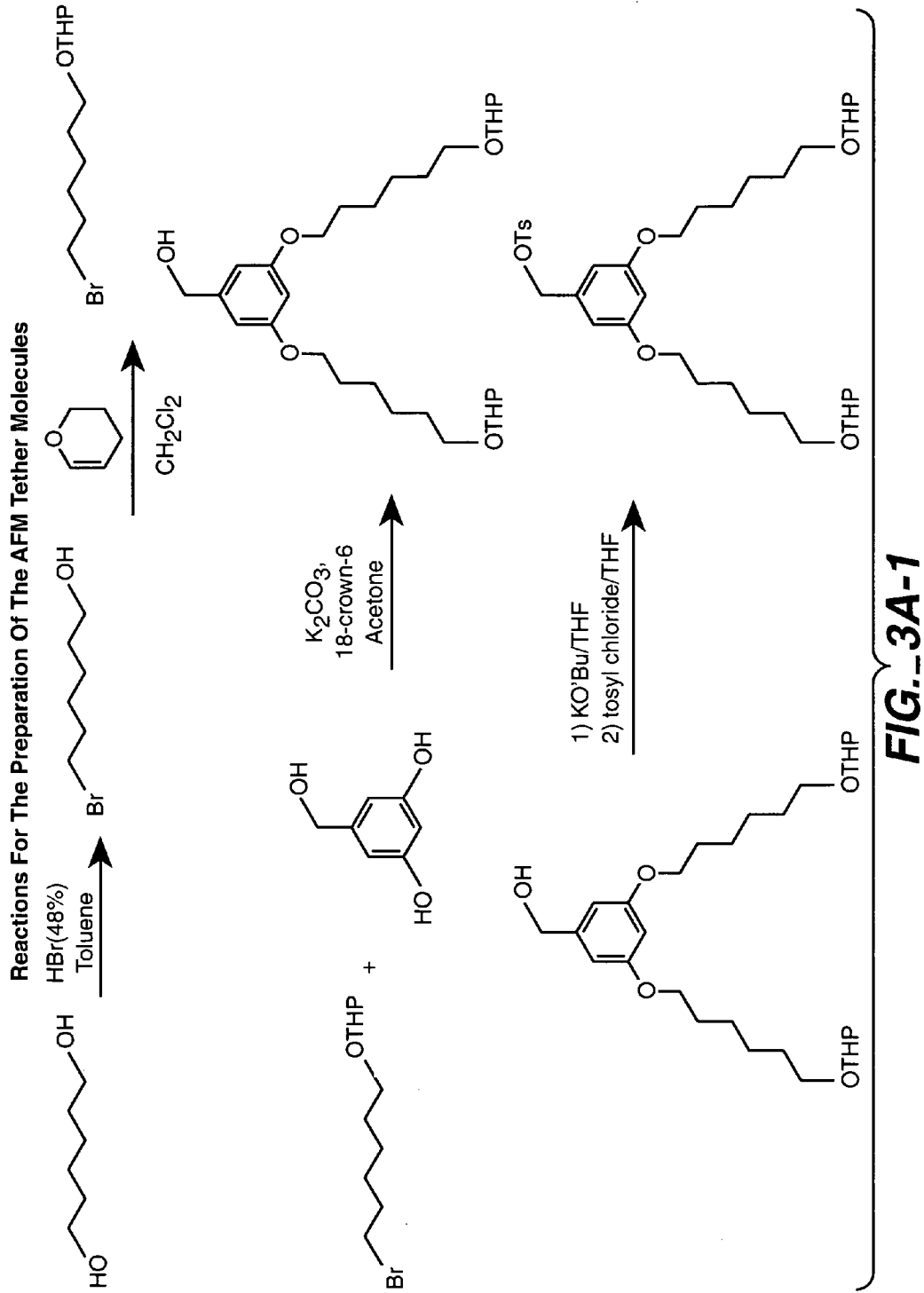
FIG._3A-1

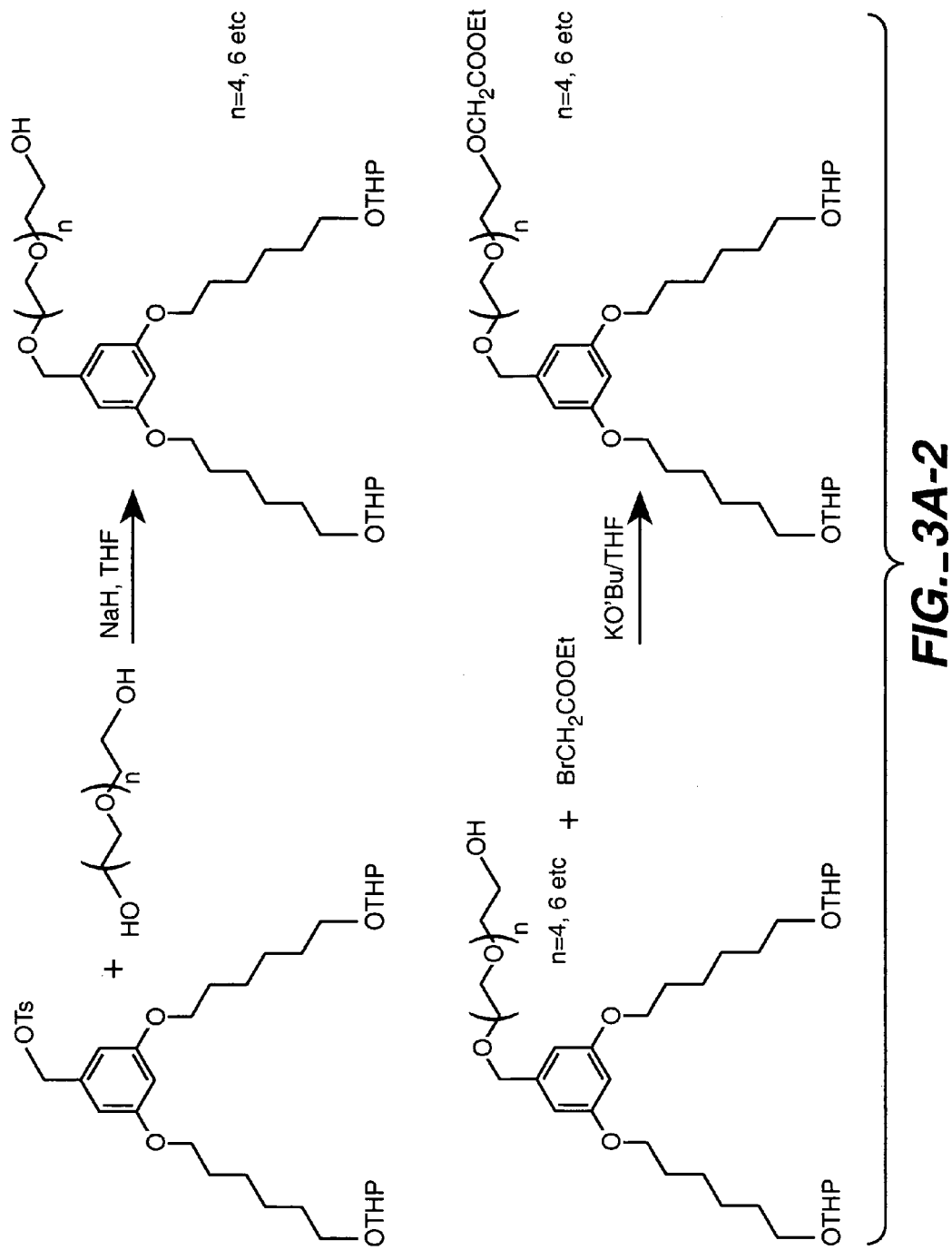
FIG._3A-2

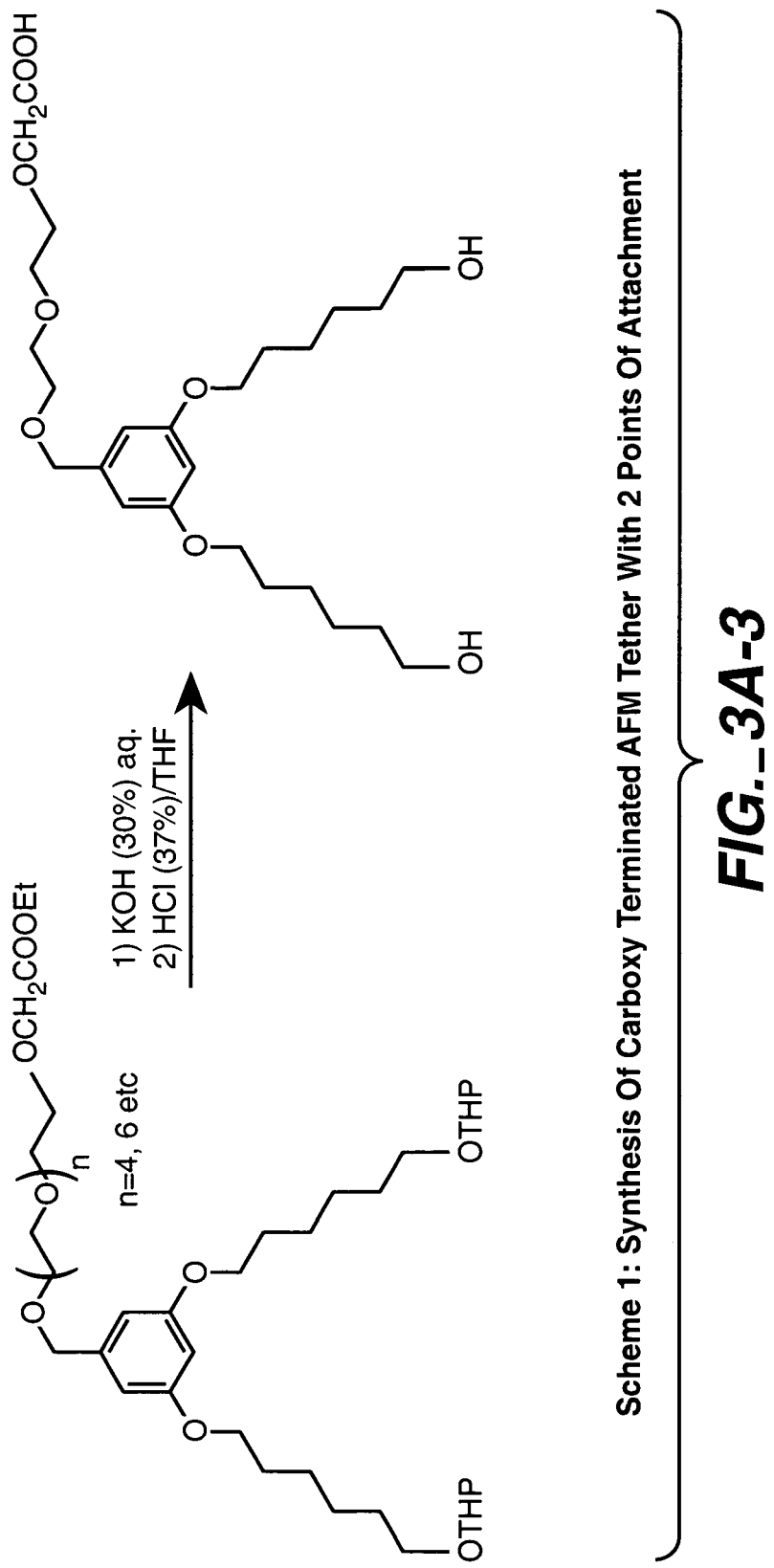
Scheme 1: Synthesis Of Carboxy Terminated AFM Tether With 2 Points Of Attachment
FIG._3A-3

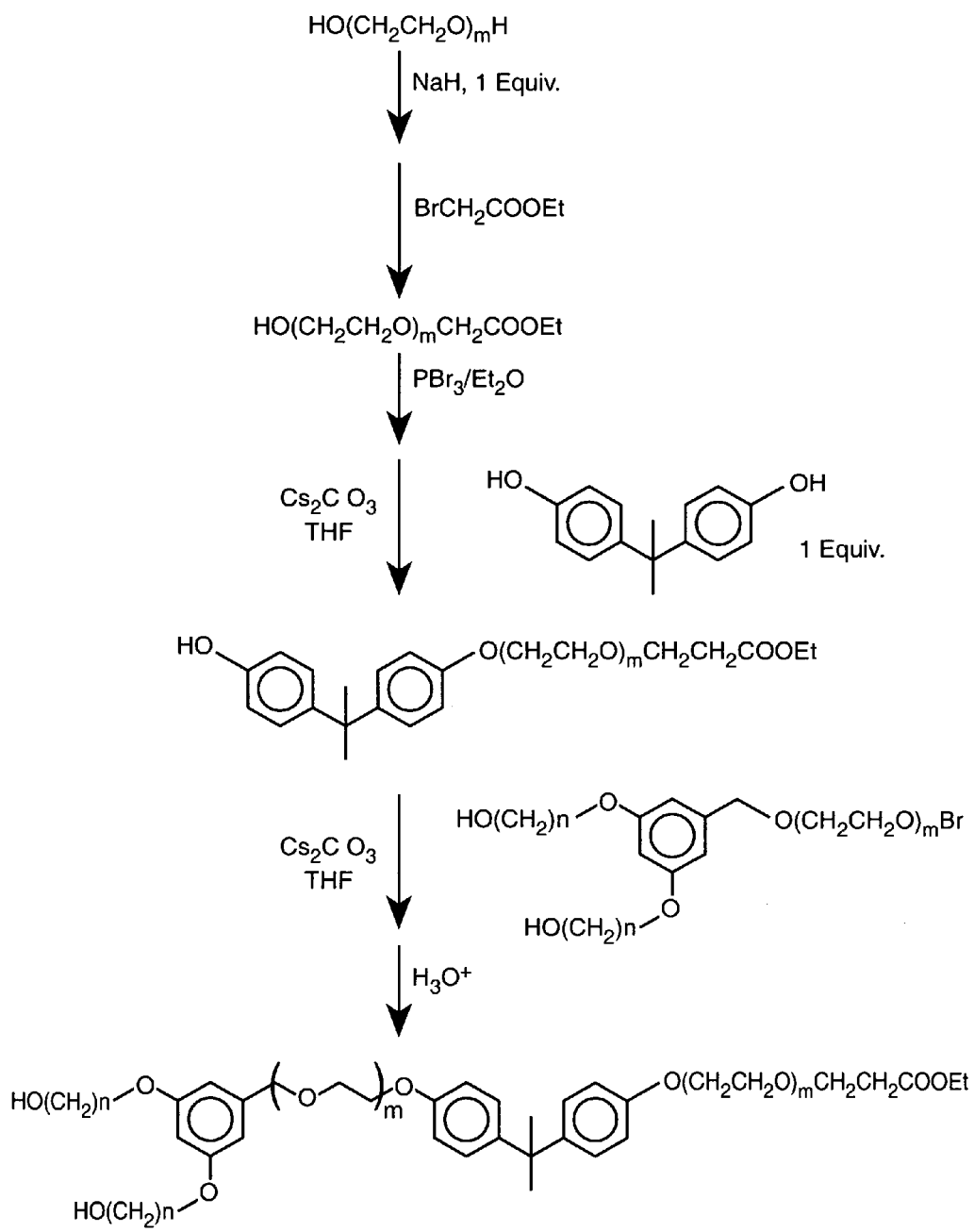
Scheme 2: Representative Synthetic Strategy For Insertion Of Rigid Rods
FIG._3B

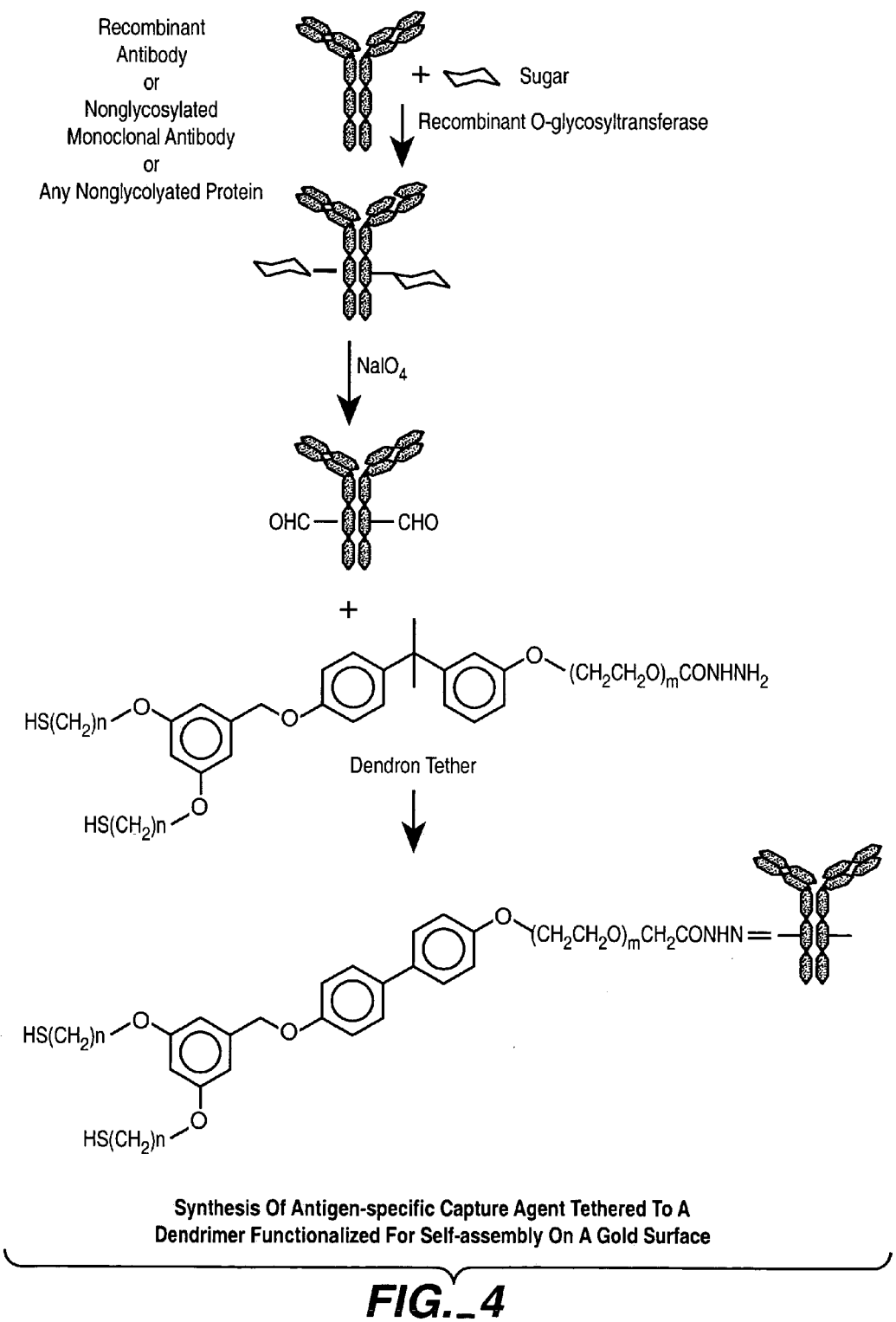
FIG._4

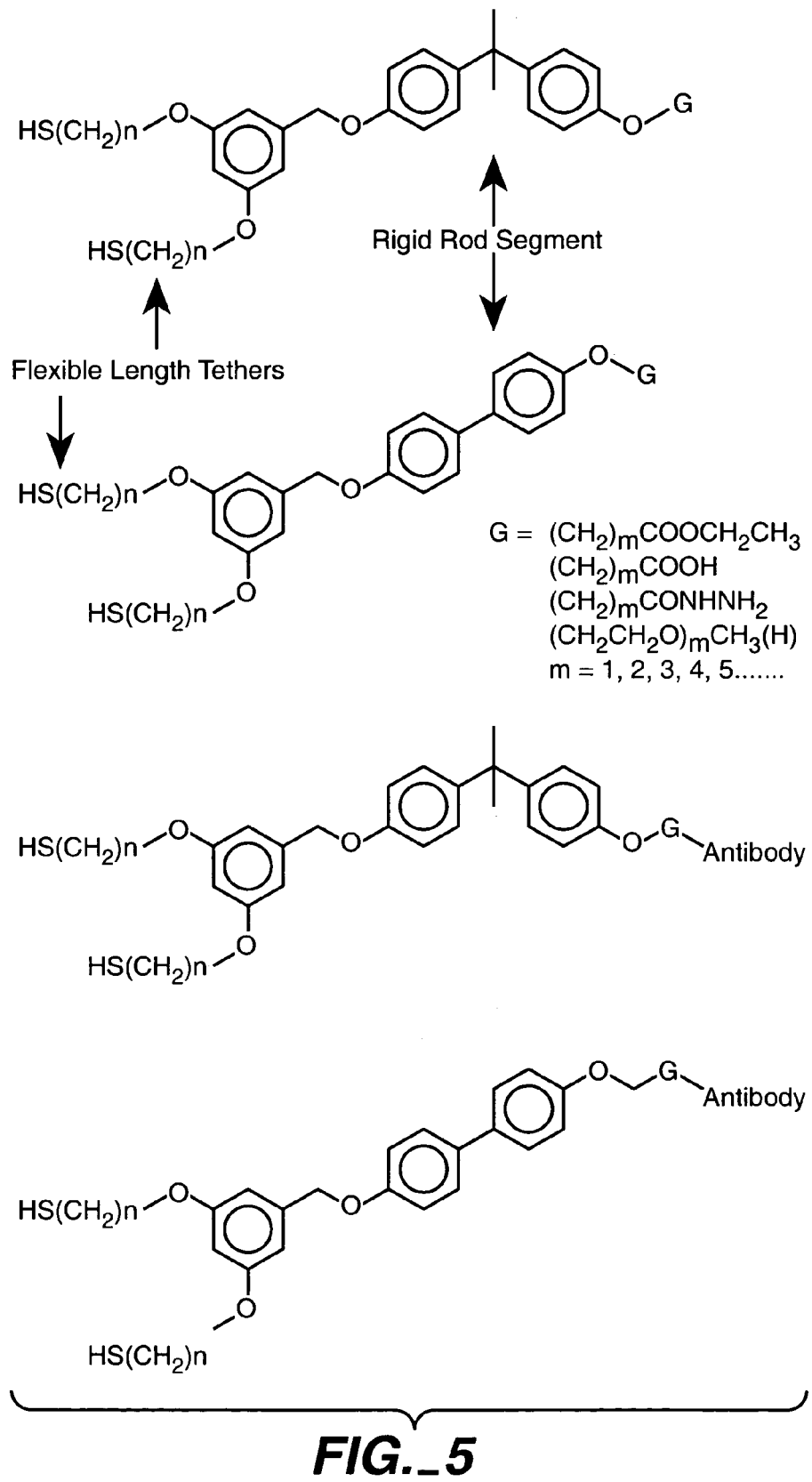
FIG._5

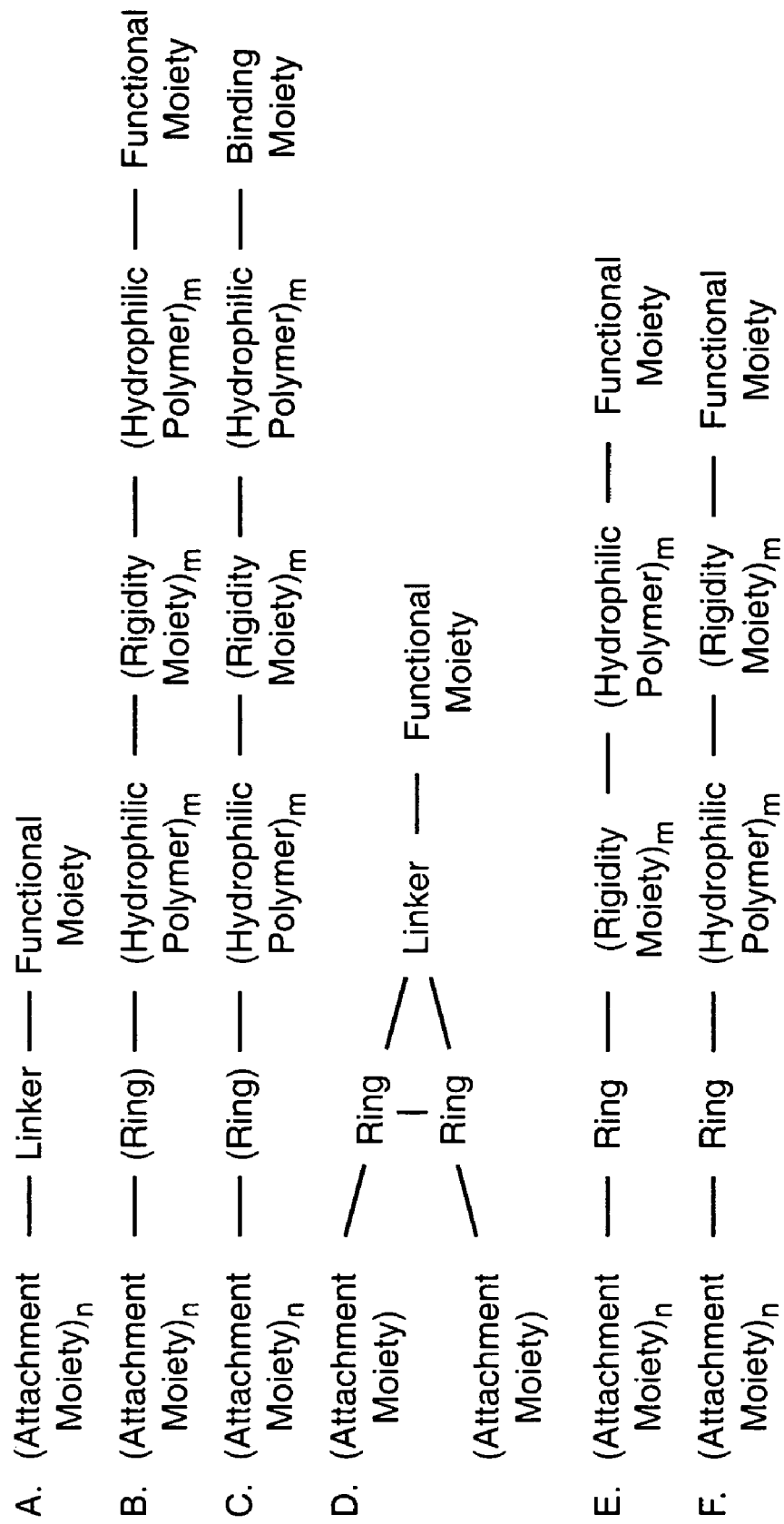
FIG._6

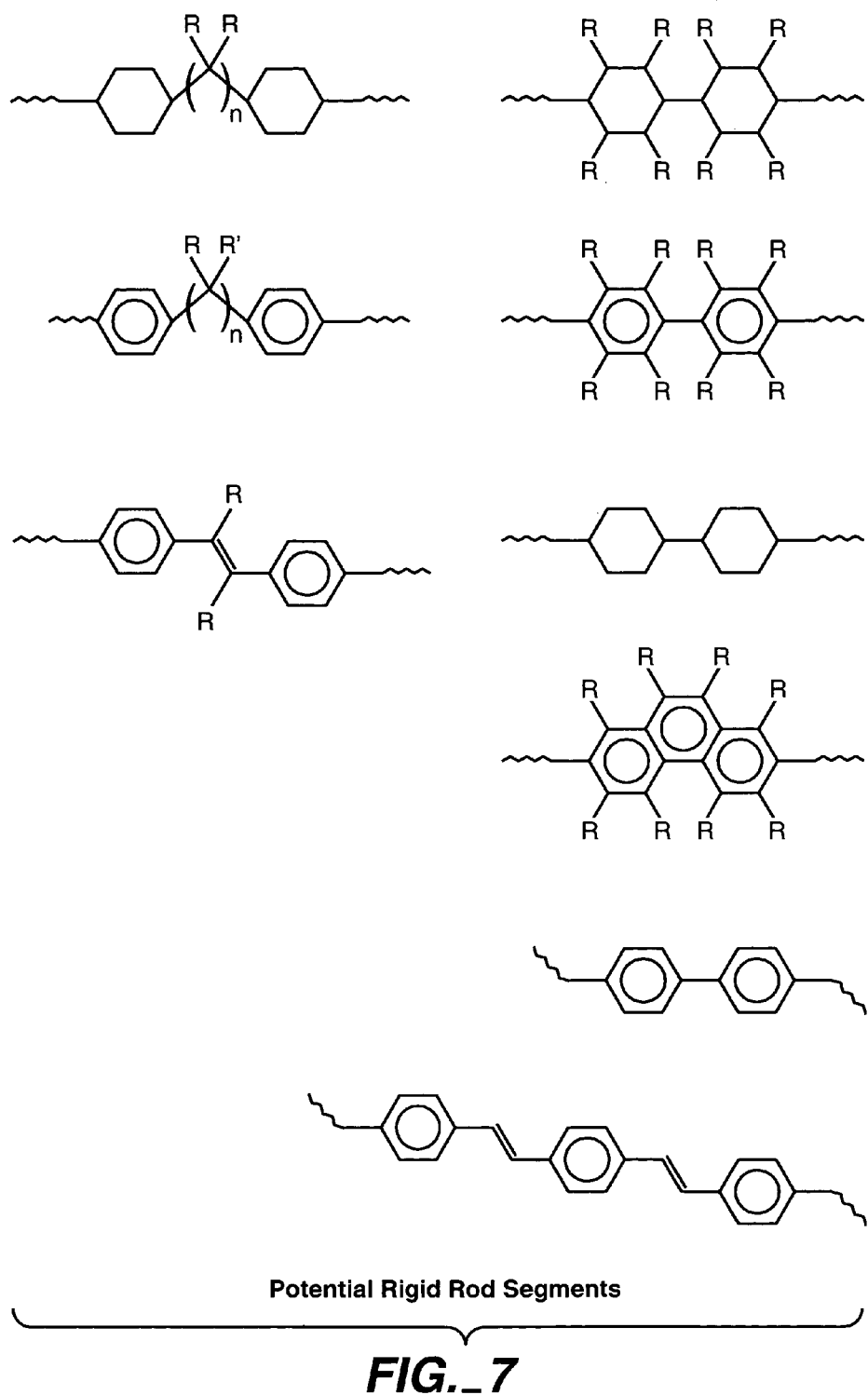
Potential Rigid Rod Segments
*FIG._7*

BIOSENSORS UTILIZING DENDRIMER-IMMOBILIZED LIGANDS AND THERE USE THEREOF

This application claims the benefit of provisional application 60/442,270, filed Jan. 23, 2003.

The invention was funded by NIH Grant No. 1 R43 A153003-01.

BACKGROUND OF THE INVENTION

In the wake of the Sep. 11, 2001 terrorist attack on the World Trade Center and the Pentagon, and the subsequent contamination of postal centers and other public buildings by anthrax spores and weapons grade anthrax aerosols, with associated deaths of postal workers and a recipient of a cross-contaminated letter, these tragic events have underlined our relative lack of rapid and effective detection protocols for both military and civilian populations. Furthermore, while it is possible to respond to a terrorist attack involving one known pathogen, such as anthrax, it is chilling to envision the potential chaos that might result from the simultaneous exposure of large segments of the general population to a multiplicity of pathogens, whether air-borne, water-borne or food-borne.

At the current time, there are no simple recognition systems that are particularly well suited to the simultaneous detection of multiple pathogenic agents. Nor are there rapid, reliable methods to identify the presence of these agents in the field, particularly for use by first responders (police, fire-fighters, paramedics, etc.). The current four-tier laboratory response network, designed to react to bioterrorism threats, proved woefully slow and cumbersome during the recent anthrax dispersion and hoax testing. For example, the first two tiers alone require at least 48 hours for identification of suspect pathogens. In addition, tiers three and four require even more sophisticated testing than tiers one and two, testing that must occur at more advanced centers, such as the Center for Disease Control and Prevention (CDC) and the US Army Medical Research Institute for Infectious Diseases (USAMRID). What is needed is a system that can be employed at the point of attack, operated by relatively untrained personnel (nonscientists), and that rapidly identifies a variety of bioterrorism agents. A recent report from NIH-NIAID (*NIAID Biodefense Research Agenda for CDC Category A Agents*, February 2002, National Institutes of Health) has identified a number of pathogens that are ideal bioterrorism agents, for example, tularemia, botulinum toxin, *Yersinia pestus* (plague), and smallpox. Notably, none of these agents are specifically detectable with currently existing detection systems.

Currently there are a wide variety of assays and sensors for the detection of the presence and/or concentration of specific substances in fluids and gases. Many of these assays and sensors rely on specific ligand/anti-ligand reactions as the mechanism of detection. In such methods, pairs of substances (i.e. the binding pairs or ligand/anti-ligands) are known to bind to each other, while binding little or not at all to other substances. For example, antibodies and their cognate antigens make up such a binding pair. Other ligand/anti-ligand binding pairs include complementary nucleic acids as well as the non-covalent interaction occurring between molecules such as biotin and streptavidin.

Detection of complexes comprising a ligand/anti-ligand binding pair is generally accomplished by labeling one component of the complex in some way, so as to make the entire complex detectable. For example, one component may be labeled with radioisotopes, fluorescent or other optically active molecules, enzymes, or virtually any other detectable moiety. In addition, other techniques are known that rely on the use of atomic force microscopy (AFM), surface plasmon resonance (SPR) or quartz crystal microbalance (QCM) systems as the means of detection.

An effective biosensor employing any of the described detection methods requires a robust flexible bioactive signal transduction system, such as one based on the attachment of specific antibodies or DNA probes to a biosensor surface. The instant invention provides multivalent dendrimer tether molecules with the capability of anchoring antibodies, or other binding moieties, to the surface of a biosensor, thus creating such a robust detection system. Furthermore, dendrimers, a class of monodisperse macromolecules with the advantage of multiple functionality, offer a number of synthetic design advantages that allow the attachment of binding moieties to a variety of surfaces to form effective biosensors (*Dendrimers and Other Dendritic Polymers*, J. M. J. Frechet and D. A. Tomalia, Eds., John Wiley & Sons, Ltd., Chichester, 2001; G. R. Newkome, C. N. Moorefield and F. Vogtle, "*Dendrimers and Dendons: Concepts Syntheses and Applications*", Wiley-VCH, Weinheim, 2001; A. W. Bosman, H. M. Janssen and E. W. Meijer, "About Dendrimers: Structure, Physical Properties and Applications, Chem. Rev. 1999, 99, 1665–1688; 0. A. Matthews, A. N. Shipway and J. Fraser Stoddart, "Dendrimers-Branching Out From Curiosities Into New Technologies", Prog. Polym. Sci. 1998, 23, 1–56. These new bioterrorism pathogen detectors are particularly well suited for use in AFM, as well as in SPR and QCM detector systems.

SUMMARY OF THE INVENTION

In accordance with the objects outlined above, the present invention provides compositions comprising a terminal dendrimer comprising at least two attachment moieties as part of a linker comprising at least one hydrophilic polymer and at least one rigidity component, as well as a functional moiety.

In another aspect the linker comprises a second hydrophilic polymer.

In a further aspect, the hydrophilic polymer comprises a polyethylene glycol polymer.

In another aspect, the linker comprises two polyethylene glycol polymer portion separated by a rigid rod portion.

In a further aspect, the invention comprises a method for formation of a binding composition, characterized by first providing a composition comprising a terminal dendrimer comprising at least two attachment moieties as part of a linker comprising at least one hydrophilic polymer and at least one rigidity component; as well as a functional moiety and attaching a binding moiety to the functional moiety.

In another aspect, the binding moiety of the method of forming a binding composition is a polypeptide.

In a further aspect, the binding moiety is an antibody or an antibody fragment.

In another aspect, the antibody or antibody fragment is recombinant.

In a further aspect, the antibody or recombinant antibody fragment is glycosylated.

In another aspect, the instant invention provides a biosensor comprising a substrate comprising a bound binding composition, where the bound composition comprises a terminal dendrimer attached to the substrate by at least two attachment moieties, a linker that comprises at least a first hydrophilic polymer and a rigidity component as well as a binding moiety.

In a further aspect, the substrate is selected from the group consisting of: metals, carbon, glass, functionalized glass, plastics, silica or silica-based materials, or cellulose.

In an additional aspect, the first hydrophilic polymer comprises a polyethylene glycol polymer.

In a further aspect, the linker comprises two polyethylene glycol polymer portions separated by a rigid rod portion.

In another aspect, the binding moiety is specific for a pathogen.

In a further aspect, the pathogen is a bacteria or a virus.

In an additional aspect the bacteria is selected from the group consisting of: *Bacillus, Vibrio*, e.g. *V. cholerae; Escherichia*, e.g. Enterotoxigenic *E. coli, Shigella*, e.g. *S. dysenteriae; Salmonella*, e.g. *S. typhi; Mycobacterium* e.g. *M. tuberculosis, M. leprae; Clostridium*, e.g. *C. botulinum, C. tetani, C. difficile, C. perfringens; Cornyebacterium*, e.g. *C. diphtheriae; Streptococcus, S. pyogenes, S. pneumoniae; Staphylococcus*, e.g. *S. aureus; Haemophilus*, e.g. *H. influenzae; Neisseria*, e.g. *N. meningitidis, N. gonorrhoeae; Yersinia*, e.g. *G. lamblia, Y. pestis, Pseudomonas*, e.g. *P. aeruginosa, P. putida; Chlamydia*, e.g. *C. trachomatis; Bordetella*, e.g. *B. pertussis*; and *Treponema*, e.g. *T. palladium*.

In an additional aspect the virus is selected from the group consisting of: orthomyxoviruses, (e.g. influenza virus), paramyxoviruses (e.g respiratory syncytial virus, mumps virus, measles virus), adenoviruses, rhinoviruses, coronaviruses, reoviruses, togaviruses (e.g. rubella virus), parvoviruses, poxviruses (e.g. variola virus, vaccinia virus), enteroviruses (e.g. poliovirus, coxsackievirus), hepatitis viruses (including A, B and C), herpesviruses (e.g. Herpes simplex virus, varicella-zoster virus, cytomegalovirus, Epstein-Barr virus), rotaviruses, Norwalk viruses, hantavirus, arenavirus, rhabdovirus (e.g. rabies virus), retroviruses (including HIV, HTLV-I and -II), papovaviruses (e.g. papillomavirus), polyomaviruses, and picornaviruses.

In an additional aspect, the instant invention provides a method of attaching a first compound to a second compound by glycosylation of the first compound with a promiscuous O-linked-glycosyltransferase, followed by oxidation of the glycosylation to produce an aldehyde-derivitized first compound and reacting the aldehyde-derivitized first compound with a hydrazide-derivitized second compound to attach the first compound to the second compound.

In a further aspect, the binding domain of the first compound is a binding moiety and the second compound is a linker.

In another aspect, the glycosylation does not decrease the binding of the binding moiety to its cognate.

In a further aspect, the instant invention provides a method of detecting a pathogen using a biosensor, wherein the biosensor comprises: a terminal dendrimer attached to said substrate by at least two attachment moieties, a linker comprising, at least a first hydrophilic polymer, a rigidity component; and a binding moiety wherein the binding moiety specifically interacts with a target analyte in a detectable manner.

In an additional aspect, the instant invention provides a method of atomic force microscopy employing a composition comprising a terminal dendrimer comprising at least two attachment moieties as part of a linker comprising at least one hydrophilic polymer and at least one rigidity component, as well as a functional moiety.

In an additional aspect, the instant invention provides a method of surface plasmon resonance employing a composition comprising a terminal dendrimer comprising at least two attachment moieties as part of a linker comprising at least one hydrophilic polymer and at least one rigidity component, as well as a functional moiety.

In an additional aspect, the instant invention provides a method of quartz crystal microbalance detection employing a composition comprising a terminal dendrimer comprising at least two attachment moieties as part of a linker comprising at least one hydrophilic polymer and at least one rigidity component, as well as a functional moiety.

DESCRIPTION OF THE DRAWINGS

FIG. 1. This figure depicts a recombinant antibody is directly conjugated to a branched dendron tether that incorporates multiple thiol (SH) groups for attachment to a gold surface of surface plasmon resonance detector.

FIG. 2. This figure depicts a bifunctional dendritic tether showing variable regions.

FIGS. 3A and 3B. These figure depicts the synthesis of a dendritic tether.

FIG. 4. This figure depicts a methodology of adding an aldehyde to an antibody.

FIG. 5. This figure depicts the synthesis of higher-order dendritic tethers.

FIG. 6. This figure depicts a number of schematics of compositions of the invention. Figure A shows attachment moieties (n is an integer of at least 2, with 2, 3 and 4 being preferred) attached to a linker. Preferred embodiments, as outlined herein, utilize any functional group that can be used for attachment to a surface of a support. The linker in A can be an alkyl or aryl group, including but not limited to cycloalkyl, heteroalkyl, substituted cyclo- or heteroalkyl, or heteroaryl, including substituted aryl and heteroalkyl, and including multi-ring structures. The functional moiety is for use for attachment to a binding moiety. B depicts a composition of attachment linkers attached to a ring structure (either cycloalkyl, aryl or multi-ring structures comprising these rings) attached to a hydrophilic polymer (m is an integer of 0 or 1). "Hydrophilic polymer" in this instance is preferably a polyethylene glycol or derivative, with glycols being particularly preferred. The hydrophilic polymer is attached to a rigidity moiety, which confers rigidity. Rigidity in this context can mean moieties that confer a steric restriction, either in degrees of freedom at any particular bond or as function of a geometric angle (e.g. holding the two ends at an angle of 180 degrees, 45 degrees, etc.). Figure C is similar with the substitution of a binding moiety for the functional moiety, which may be true for any of the structures outlined herein. Figure D shows attachment moieties attached to different rings of a multiring structure such as a biphenyl group, etc. The linker in this embodiment may also include hydrophilic polymers and rigidity moieties. Figures E and F depict dendrimeric compositions with one rigidity moiety and one hydrophilic moiety.

FIG. 7. This figure depicts a variety of suitable rigidity moieties. Suitable R substitutions are described herein.

DETAILED DESCRIPTION OF THE INVENTION

The present invention is directed to methods and compositions useful as biosensors that specifically interact with various pathogens and other target analytes. The biosensor itself, comprises functionalized dendritic tethers derivatized for attachment to a variety of surfaces as self-assembled monolayers (SAMs) as well as attached binding moieties (sometimes referred to as capture binding ligands). The specificity of the biosensor is provided by the attachment of the target-specific binding moiety to the derivitized dendritic tethers. The use of these dendritic tethers allows the formation of robust thin film biosensors that can be employed in a variety of detection systems, including but not limited to, AFM or as part of a SPR or QCM detection system. Dendrimers incorporating binding moieties specific to individual or multiple pathogens can also be formulated for incorporation into chromatographic or microarray ensembles. Accordingly, the present invention provides compositions comprising supports comprising surfaces to which the binding moieties (e.g. antibodies) are attached for the detection of target analytes (e.g. pathogens) as well as methods and compositions relating to the attachment of such binding moieties.

Accordingly, the present invention provides compositions and methods for detecting the presence or absence of target analytes, such as the pathogens described above, in a sample. As will be appreciated by those in the art, the sample solution may comprise any number of things, including, but not limited to, bodily fluids (including, but not limited to, blood, urine, serum, lymph, saliva, anal and vaginal secretions, perspiration and semen, of virtually any organism, with mammalian samples being preferred and human samples being particularly preferred); environmental samples (including, but not limited to, air, agricultural, water and soil samples); biological warfare agent samples; research samples; and raw samples (bacteria, virus, genomic DNA, etc.); As will be appreciated by those in the art, virtually any experimental manipulation may have been done on the sample.

Thus the present invention is directed to methods and compositions for the detection of target analytes in test samples. By "target analyte" or "analyte" or grammatical equivalents herein is meant any molecule, compound or particle to be detected. As outlined below, target analytes preferably bind to binding ligands, as is more fully described below. As will be appreciated by those in the art, a large number of analytes may be detected using the present methods; basically, any target analyte for which a binding ligand, described below, may be made may be detected using the methods of the invention.

Suitable analytes include organic and inorganic molecules, including biomolecules. In a preferred embodiment, the analyte may be an environmental pollutant (including pesticides, insecticides, toxins, etc.); a chemical (including solvents, polymers, organic materials, etc.); therapeutic molecules (including therapeutic and abused drugs, antibiotics, etc.); biomolecules (including hormones, cytokines, proteins, lipids, carbohydrates, cellular membrane antigens and receptors (neural, hormonal, nutrient, and cell surface receptors) or their ligands, etc); whole cells (including procaryotic (such as pathogenic bacteria) and eukaryotic cells, including mammalian tumor cells); viruses (including retroviruses, herpesviruses, adenoviruses, lentiviruses, etc.); and spores; etc. Particularly preferred analytes are environmental pollutants; nucleic acids; proteins (including enzymes, antibodies, antigens, growth factors, cytokines, etc); therapeutic and abused drugs; cells; and viruses.

In a preferred embodiment, the target analytes are not nucleic acids.

Of particular relevance to the biosensor compositions and methods of the instant invention are a variety of pathogens outlined in a the recent report by NIH-NIAID cited above.

Each the cited pathogens could be employed as bioterror weapons against military and civilian targets. These potential bioterror agents include: *Bacillus anthracis* (anthrax) toxin, *Yersinia pestus* (plague), botulinum toxin, tularemia (*Francisella tularensis*) and smallpox virus.

In addition to the pathogens specifically outlined as potential bioterror agents, the instant technology may also be employed to detect both common and uncommon bacterial, viral and parasitic food-borne and water-borne pathogens, as defined by the Center for Disease Control and Prevention (P. S. Mead, L. Slutskeer, V. Dietz, L. McCaig, J. S. Breese, C. Shapiro, P. M. Griffin and R. V. Tauxe, "Food-Related Illness and Death in the United States", Emerging Infectious Diseases, 1999, 5, 607–625), including but not limited to, *Campylobacter* spp., *Clostridium perfringens*, *Escherichia coli* O157:H7, *E. coli*, non-O157 STEC, *E. coli*, enterotoxigenic, *E. coli*, other diarrhenogenic, *Listeria monocytogenes*, *Salmonella Typhi*, *Salmonella*, nontyphoidal, *Shigella* spp., *Staphylococcus aureus* and its toxin, *Streptococcus* sp, *Vibrio cholerae*, toxigenic, *Vibrio*, other, *Yersinia enterocolitica*, *Cryptosporidium parvum*, *Cyclospora cayetanensis*, *Giardia lamblia*, *Toxoplasma gondii*, *Trichinella spiralis*, Norwalk-like viruses, Rotavirus, Astrovirus, and Hepatitus A.

Furthermore, the technology of the instant invention is capable of detecting bioengineered pathogens. Such detection only requires that a specific binding moiety for the bioengineered pathogen be isolated and immobilized on a dendritic tether as a SAM for use in AFM or in an SPR or QCM detector. For example, an antibody specific to a particular bioengineered pathogen could be generated, using methods well known in the art, and attached to the derivitized dendritic tethers of the instant invention and used for the detection of that pathogen.

In addition to the pathogens described above, many other viruses may be detected using the biosensors of the instant invention. Such viruses include, but are not limited to, orthomyxoviruses, (e.g. influenza virus), paramyxoviruses (e.g respiratory syncytial virus, mumps virus, measles virus), adenoviruses, rhinoviruses, coronaviruses, reoviruses, togaviruses (e.g. rubella virus), parvoviruses, poxviruses (e.g. variola virus, vaccinia virus), enteroviruses (e.g. poliovirus, coxsackievirus), hepatitis viruses (including A, B and C), herpesviruses (e.g. Herpes simplex virus, varicella-zoster virus, cytomegalovirus, Epstein-Barr virus), rotaviruses, Norwalk viruses, hantavirus, arenavirus, rhabdovirus (e.g. rabies virus), retroviruses (including HIV, HTLV-I and -II), papovaviruses (e.g. papillomavirus), polyomaviruses, and picomaviruses, and the like. Examples of the wide variety of pathogenic and non-pathogenic prokaryotes amenable to detection by the instant invention are, *Bacillus*, *Vibrio*, e.g. *V. cholerae*; *Escherichia*, e.g. Enterotoxigenic *E. coli*, *Shigella*, e.g. *S. dysenteriae*; *Salmonella*, e.g. *S. typhi*; *Mycobacterium* e.g. *M. tuberculosis*, *M. leprae*; *Clostridium*, e.g. *C. botulinum*, *C. tetani*, *C. difficile*, *C. perfringens*; *Cornyebacterium*, e.g. *C. diphtheriae*; *Streptococcus*, *S. pyogenes*, *S. pneumoniae*; *Staphylococcus*, e.g. *S. aureus*; *Haemophilus*, e.g. *H. influenzae*; *Neisseria*, e.g. *N. meningitidis*, *N. gonorrhoeae*; *Yersinia*, e.g. *G. lamblia*, *Y. pestis*, *Pseudomonas*, e.g. *P. aeruginosa*, *P. putida*; *Chlamydia*, e.g. *C. trachomatis*; *Bordetella*, e.g. *B. pertussis*; *Treponema*, e.g. *T. palladium*; and the like.

The compositions of the present invention comprise dendritic tethers, that is, a dendridic structure useful for attachment of the binding ligands to the surface. These dendrimers are highly branched, monodisperse macromolecules that exhibit repeating structure radiating from a well-defined core structure. The dendrimers have unique properties of well-ordered structures, enhanced solubility and processibility, and the capability of having well-defined and controlled functionality, particularly at the dendrimer periphery. Their use in a wide variety of applications, ranging from photonics to medicine, has been well documented. However, their potential for use as heterobifunctional SAMs for use in AFM or such detector instrumentation as SPR and QCM systems has not been exploited. In the present invention, dendritic tethers with at least three "arms" (e.g. two for attachment to the surface and one for the binding moiety either directly or through a linker) are preferred, although additional "arms" can also be used.

The dendrimeric compositions of the present invention generally comprise three components: a terminal dendrimer, used ultimately to attach to a surface using at least two attachment moieties; a linker, optionally comprising at least one hydrophilic polymeric section and a rigidity component; and a functional moiety used for attachment of a binding moiety (sometimes referred to herein as a "binding moiety" or a "capture moiety").

In a preferred embodiment, the rigidity of the dendritic tethers of the instant invention can be controlled. Thus, in a preferred embodiment, the dendritic tethers comprise monodisperse macromolecules containing flexible linear, rigid-rod and dendritic segments which offer unique design capabilities that allow position of a variety of binding moieties through multivalent attachment functionalities while controlling the ultimate flexibility of the tether. These types of constructs are preferably functionalized at one terminus for attachment to an AFM tip, or other detection system. Similarly, the other terminus is preferably functionalized for covalent coupling of binding moieties, e.g. proteins, peptides, or organic small molecules, and such binding moieties may be varied independently of one another and be connected to each other through spaces with varying degrees of rigidity. A general example of such moieties is depicted in the Figures.

In a preferred embodiment, the dendritic tethers comprise at least one hydrophilic polymeric section. In a particularly preferred embodiment, the hydrophilic polymeric section is comprised of polyethylene glycol (PEG) with glycol polymers being preferred. Insertion of such PEG polymers is particularly preferred as they are known in the art to inhibit non-specific binding. Additionally, preferred embodiments comprise more than one hydrophilic polymeric section and an intervening rigid rod section. Such multiple hydrophilic polymeric sections are preferably PEG, however, each section need not have identical numbers of ethylene glycol units.

In a preferred embodiment, the dendritic tethers comprise combinations of alkyl and aryl groups. By "alkyl group" or grammatical equivalents herein is meant a straight or branched chain alkyl group, with straight chain alkyl groups being preferred. If branched, it may be branched at one or more positions, and unless specified, at any position. The alkyl group may range from about 1 to about 30 carbon atoms (C1–C30), with a preferred embodiment utilizing from about 1 to about 20 carbon atoms (C1–C20), with about C1 through about C12 to about C15 being preferred, and C1 to C5 being particularly preferred, although in some embodiments the alkyl group may be much larger. Also included within the definition of an alkyl group are cycloalkyl groups such as C5 and C6 rings, and heterocyclic rings with nitrogen, oxygen, sulfur or phosphorus. Alkyl also includes heteroalkyl, with heteroatoms of sulfur, oxygen, nitrogen, and silicone being preferred. Alkyl includes substituted alkyl groups. By "substituted alkyl group" herein is meant an alkyl group further comprising one or more substitution moieties, as defined below.

By "aryl group" or grammatical equivalents herein is meant an aromatic monocyclic or polycyclic hydrocarbon moiety generally containing 5 to 14 carbon atoms (although larger polycyclic rings structures may be made) and any carbocylic ketone or thioketone derivative thereof, wherein the carbon atom with the free valence is a member of an aromatic ring. Aryl groups include arylene groups and aromatic groups with more than two atoms removed. For the purposes of this application aryl includes heterocycle. "Heterocycle" or "heteroaryl" means an aromatic group wherein 1 to 5 of the indicated carbon atoms are replaced by a heteroatom chosen from nitrogen, oxygen, sulfur, phosphorus, boron and silicon wherein the atom with the free valence is a member of an aromatic ring, and any heterocyclic ketone and thioketone derivative thereof. Thus, heterocycle includes thienyl, furyl, pyrrolyl, pyrimidinyl, oxalyl, indolyl, purinyl, quinolyl, isoquinolyl, thiazolyl, imidozyl, etc. Substituted aryl groups are also included.

Suitable substitution groups (sometimes depicted herein as "R" groups) include, but are not limited to, hydrogen, alkyl, alcohol, aromatic, amino, amido, nitro, ethers, esters, aldehydes, sulfonyl, silicon moieties, halogens, sulfur containing moieties, phosphorus containing moieties, and ethylene glycols.

Preferably, the dendritic tethers include attachment moieties for attachment to the surface. As will be appreciated by those in the art, the attachment moiety will depend in part on the chemistry and composition of the surface. In a preferred embodiment, the surface is gold and the attachment moieties comprise thiols. In another preferred embodiment, the surface is an AFM tip and the attachment moieties comprise hydoxyls. As will be appreciated in the art, a wide variety of attachment moieties can be utilized, depending on the surface to which it will be attached, for example, silanes, phosphonates, etc., can all be used.

The dendritic tethers can be synthesized by standard procedures (*Dendrimers and Other Dendritic Polymers*, J. M. J. Frechet and D. A. Tomalia, Eds., John Wiley & Sons, Ltd., Chichester, 2001; G. R. Newkome, C. N. Moorefield and F. Vogtle, *Dendrimers and Dendons: Concepts, Syntheses and Applications*", Wiley-VCH, Weinheim, 2001; A. W. Bosman, H. M. Janssen and E. W. Meijer, "About Dendrimers: Structure, Physical Properties and Applications", Chem. Rev. 1999, 99, 1665–1688; 0. A. Matthews, A. N. Shipway and J. Fraser Stoddart, "Dendrimers-Branching Out From Curiosities Into New Technologies", Prog. Polym. Sci. 1998, 23, 1–56) as illustrated in FIG. 3. In this scheme, the ellipsoidal moieties represent a variety of linker groups, such as long chain alkyls, which serve to control the spacing of the reactive functionalities above the gold surface. Binding moieties such as polyclonal antibodies can be modified readily for attachment to dendrimers through their unique glycosylation sites. However, since recombinant antibodies and many monoclonal antibodies are not glycosylated, they must be derivatized for attachment to the dendrimer. Accordingly, a dendritic tether with one arm functionalized with a hydrazide moiety has been developed to overcome this obstacle. The hydrazide-functionalized dendrimer arm is reacted with an aldehyde functionality derived from a sugar conjugated to the recombinant binding moiety of interest to allow for covalent attachment. The opposing dendrimer arm incorporates multiple thiol (SH) groups, depending on dendrimer generation, for attachment, for example, to a gold SPR detector surface. A unique methodology for the derivatization of a recombinant binding moiety, such as an antibody, with the required aldehyde (CHO) group, is illustrated in FIG. 4.

Dendron structures (generations) can be synthesized that incorporate multiple thiol (SH) attachment groups. When incorporated into the final dendrimer construct, the higher level generations containing greater numbers of thiol groups yield SAMs that are much more robust under flow conditions, thereby greatly increasing the lifetime of the detector devices for pathogen detection. The synthetic approach to these higher generations is illustrated in FIG. 5. Thus, preferred embodiments utilize 2, 3, 4 or 5 attachment moieties, which can be the same or different.

For a typical biosensor construct, the dendritic tether illustrated in FIG. 2 is attached to a surface as a self-assembled monolayer (SAM). By "monolayer" or "self-assembled monolayer" or "SAM" herein is meant a relatively ordered assembly of molecules spontaneously chemisorbed on a surface, in which the molecules are oriented approximately parallel to each other and roughly perpendicular to the surface. A majority of the molecules includes a functional group that adheres to the surface, and a portion that interacts with neighboring molecules in the monolayer to form the relatively ordered array. A "mixed" monolayer comprises a heterogeneous monolayer, that is, where at least two different molecules make up the monolayer. For example, in the present invention, one SAM species can comprise the dendrimeric composition, and a second species can comprise an alkyl chain, or a hydrophilic polymer species similar to that contained in the dendrimeric composition. Previous self-assembled monolayer constructs have been used in a variety of formats, primarily with single-stranded long-chain alkylthiols having a single attachment functionality for surface plasmon resonance measurements and some designed for molecular electronics applications (V. Chechik, R. M. Crooks and C. J. M. Stirling, "Reactions and Reactivity in Self-Assembled Monolayers", Adv. Mater. 2000, 12, 1161; S. Flink, F. C. J. M. van Veggel and D. Reinhoudt, "Sensor Functionalities in Self-Assembled Monolayers", Adv. Mater. 2000, 12, 1315; T. Neumann, M. -L. Johansson, D. Kambhampati and W. Knoll, "Surface-Plasmon Fluorescence Spectroscopy", Adv. Funct. Mater. 2002, 12, 575. However, monodisperse multi-arm dendrimers with multiple attachment functionalities can provide greatly enhanced structural stability in SAMs. Previous work by other groups have described SAMs on gold consisting of pre-formed fourth generation poly(amidoamine) (PAMAM) dendrimers having terminal groups functionalized with thiol groups by addition of mercaptodecanoic acid. Such SAMs have distinct disadvantages because they consist of commercial dendrimers that are not monodisperse (they are mixtures). Consequently these dendrimers contain a varying number of terminal functionalities leading to the formation of irregular surfaces. In addition to being imperfect, and not readily tailorable to specific bioactive molecules, they must be tethered to a long alkyl chain associated with the gold surface. The necessary use of this long tether dictates that the active site is actually quite far from the gold sensory surface, leading to a viscoelastic effect on a quartz crystal microbalance (See Ref. 3, Section D. "The Behavior of Dendrimers on Surfaces and in Amphiphilic Materials", and references therein.) and to nonlinear readings on a surface plasmon resonance sensor. (C. Nylander, B. Liedberg and T. Lind, "Gas Detection by Means of Surface Plasmon Resonance", Sensors and Actuators, 1982/3, 3, 79; C. Jeppesen, J. Y. Wong, T. L. Kuhl, J. N. Israelachvili, N. Mulach, S. Zaplipsky and C. N. Marques, "Impact of Polymer Tether Length on Multiple L:igand-Receptor Bond Formation", Science, 2001, 293, 265.) Jeppesen et al. have most recently described the impact and significance of the length and configuration of the tether groups on ligand-bond formation. Their detailed analysis of the implications of using flexible long single-chain tethers, by Monte Carlo simulations, diffusion reaction theory, and surface force measurements, lead to the startling conclusion that the tether groups do not usually exist in the highly extended configurations necessary for efficient binding between, for example, biotin attached to the tether, and streptavidin (a common construct used in biosensors). While this dictates that the tether can stretch to attach to a target, it also points to the fact that the more rigid dendrimer scaffolds of the instant invention provide a faster and more effective binding scenario by eliminating the conformational re-ordering that is a necessary initial step with more flexible tethers. This analysis holds out that increased speed and sensitivity in target binding is possible by designing order and "rigidity" into the detecting surface as is described above with regard to the dendritic tethers of the instant invention.

The biosensors of the instant invention utilize a substrate as the site of SAM formation. By "substrate" or "solid support" or other grammatical equivalents herein is meant any material that can be modified to contain the compositions of the invention, generally discrete individual sites appropriate for the attachment or association of the binding ligands, and is amenable to at least one detection method, including, but not limited to, AFM, SPR or QCM. In some embodiments, one of the assay components can be labeled as described herein.

As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon, carbon, metals, particularly gold, inorganic glasses and a variety of other polymers. In addition, the substrate has a surface, which can comprise the same material as the support or an added layer, added layers, or multiple spots. For example, the support may be made of a plastic and the surface(s) are made of a metal such as gold.

In addition, so-called "green" technologies are compatible with the instant invention. For example, in a preferred embodiment, the substrate is comprised of cellulose processed as described in U.S. Patent Application 20030157351 to Swatloski, R., Rogers, R., and Holbrey, J. (hereby incorporated in it's entirety) or any other suitable renewable compound. Particularly preferred are renewable compounds processed without the use of harmful or volatile organic solvents.

Generally the substrate will be flat (planar), although as will be appreciated by those in the art, other configurations of substrates may be used as well.

In addition, the supports can be part of a cartridge, particularly disposable cartridges, that can be inserted into a detection device. Cartridges are generally made of the same materials as outlined for supports, although this is not required, and may include biocoatings or biopolymers or other additives to reduce non-specific binding of assay components to parts of the cartridge. In addition, the cartridge may contain any number of other assay components, including proteins, nucleases or nuclease inhibitors, proteases or protease inhibitors, buffers, salts, chelators, etc.

In some embodiments, the compositions comprise an array. Such arrays may be formed via a large number of different methods. In a preferred embodiment, a single support or single surface is segregated, either physically, chemically or spatially into discrete locations (e.g. "cells" or "addresses" or "pads"). Alternatively, the array may be made by providing a number of discrete surfaces on the support; e.g. an array of gold areas or spots. In general, a support comprising an "array" contains at least two distinct capture ligands (e.g. antibodies), further defined below. As will be appreciated by those in the art, an array may comprise from two to up to hundreds or thousands of discrete locations, depending on the size of the desired device, its utility, its compositions, etc.

The biosensors of the present invention comprise binding moieties. By "binding moieties", "binding ligands" or "capture ligands" herein is meant a moiety that is attached to the surface using the compositions outlined herein that will bind to a target analyte, e.g. pathogenic bacteria. As will be appreciated by those in the art, the composition of the binding moiety will depend on the composition of the target analyte. Binding moieties for a wide variety of analytes are known or can be readily found using known techniques. For example, when the analyte is a protein, the binding moieties include proteins (particularly including antibodies or fragments thereof (FAbs, etc.)) or small molecules.

In a preferred embodiment, the binding moiety is a protein. A variety of systems for the identification of protein—protein interactions are known, including the yeast two-hybrid and phage display systems.

In a preferred embodiment, the binding moieties comprises an antibody. The term "antibody" includes antibody fragments, as are known in the art, including Fab, Fab2, single chain antibodies (Fv for example), chimeric antibodies, etc., either produced by the modification of whole antibodies or those synthesized de novo using recombinant DNA technologies.

The antibodies may be polyclonal or monoclonal. Monoclonal antibodies are directed against a single antigenic site or a single determinant on an antigen. Thus monoclonal antibodies, in contrast to polyclonal antibodies, which are directed against multiple different epitopes, are very specific. Monoclonal antibodies are usually obtained from the supernatant of hybridoma culture (see Kohler and Milstein, Nature 256:495–7 (1975); Harlow and Lane, Antibodies: A Laboratory Manual (New York: Cold Spring Harbor Laboratory Press, 1988). The antibodies may be naturally occurring or synthetic, and may be from any convenient organism, including rodents (mice and rats particularly), rabbits, goats, etc. If desired, the antibodies may be humanized as is well known in the art. In addition, antibodies (including Ab fragments) can be derivitized with additional moieties such as PEG, as is well known in the art.

The binding moieties will specifically bind to a target. By "specifically bind" herein is meant that the binding moiety will bind to the target with sufficient specificity to uniquely identify the target in the sensor. In a preferred embodiment, the binding has a binding constant in the range of at least $10^{-4}$–$10^{-6}$, with a preferred range being $10^{-7}$–$10^{-9}$ $M^{-1}$.

The method of attachment of the binding moiety to the functional moiety of the dendritic tether will generally be done as is known in the art, and will depend on both the composition of the functional moiety and the binding ligand. In general, the moieties are attached through the use of functional groups on each that can then be used for attachment. Preferred functional groups for attachment are amino groups, carboxy groups, oxo groups and thiol groups. These functional groups can then be attached, either directly or indirectly through the use of an additional linker. Linkers are well known in the art; for example, homo- or hetero-bifunctional linkers as are well known (see 1994 Pierce Chemical Company catalog, technical section on cross-linkers, pages 155–200, incorporated herein by reference).

Coupling of the binding moieties can be accomplished using a wide variety of methods. In a preferred embodiment, binding moieties such as polypeptides, antibodies or other organic molecules, are attached covalently to the compositions. Such covalent coupling can be effected via methods well known in the art. For example, the binding moiety may have an exposed aldehyde moiety capable of reacting with a hydrazide of the dendritic tether. In a preferred embodiment the aldehyde moiety is present as the result of the oxidation of a glycoslyation at a specific position of the binding moiety.

In a preferred embodiment, the binding moiety is a molecule that contains no native glycoslyations. Such a molecule is artificially glycoslyated, and subsequently oxidized, in order to provide an exposed aldehyde for coupling any appropriate cognate molecule or to the dendritic tethers of the instant invention. Artificial glycoslyation may be accomplished by any number of means well known in the art. For example, polypeptides that have appropriate amino sequences can be glycoslyated, under physiological conditions, by native O-linked GlcNac Transferase. (See Lubas and Hannover, J. Biol. Chem., 275(15) 2000 10983–10988; Kreppel et al., J. Biol. Chem., 272(14) 1997 9308–9315.)

In a preferred embodiment, a promiscuous variant of O-linked GlcNac Transferase (OGT) is employed to glycoslyate the binding moiety of the instant invention. This promiscuous variant was created by excising the nucleotides responsible for encoding the substrate-specificity domain of a native OGT polypeptide from the coding sequence of the enzyme. Accordingly, a wide variety of polypeptides may now be glycosylated which were previously incapable of acting as a substrate for the native OGT. Similar to the native OGT, the promiscuous variant also has the advantage of glycoslyating its substrate under physiological conditions, thus denaturation of the binding moiety is not necessary. Once a binding moiety is glycoslyated by the promiscuous OGT variant, it may then be oxidized and coupled to a hydrazide containing dendritic tether, or other molecule, as described above.

In a preferred embodiment the binding pocket or active site of the binding moiety is not the site of glycoslyation. Protection of the binding pocket or active site of the binding moiety can be accomplished by a variety of means. For example, the binding moiety may initially be bound to a chromatographic substrate comprised of the binding moiety's cognate. While bound to the chromatographic substrate, the binding moiety can then be glycoslyated. Such glycoslyation thus safely avoids modification of those functional groups necessary for cognate binding. The binding moiety may then be separated from the chromatographic substrate by methods well known in the art, e.g. increase in ionic concentration, addition of competitive binding moieties, etc., and oxidized for coupling.

In addition, the functional OGT fragment can be used to attach a sugar reside to any free hydroxyl group, thus enabling the attachment of two components. For example, moieties with free hydroxyl groups (including small molecules and proteins (including polypeptides and peptides), chemical species such as polymers, substituted alkyl groups, glycols, etc.) can be contacted with a functional OGT fragment to add a sugar, which then can be used as a functional moiety for attachment to a second component (again, a small molecule, protein, chemical species, etc.). As outlined above, it may be desirable to protect certain hydroxyl groups on the first component to prevent the loss of biological activity. Suitable protecting groups are known in the art, see Greene, Protecting Groups, supra.

Atomic Force Microscopy is a powerful tool for detection of ligand/anti-ligand binding events. (See, Hinterdofer, et al., "Surface Attachment of Ligands and Recptors for Molecular Recognition Force Technology" Colloids and Surfaces B: Biointerfaces, 23 2002 115–123.) The basic strategy employed in AFM is to first attach a binding mioety to an AFM tip (available commercially from producers such as Park, Sunnyvale, Calif.; or Maclevers, Molecular Imaging, Phoenix, Ariz.), and a target analyte to a substrate. The tip then proceeds through a force-distance cycle, wherein it initially approaches the substrate to allow for ligand/anti-ligand binding between the binding moiety and the target analyte. Once sufficient time has elapsed to allow for the interaction to occur, the tip is retracted. The retraction continues with increasing force until the interaction between the binding moiety and the target analyte is broken. The force necessary to break the interaction between the binding moiety and target analyte is termed the "unbinding force." Using this strategy it is possible to detect single molecule recognition events, e.g. antibody-antigen or sense-antisene DNA interactions.

The general strategy of AFM can be tailored for specific uses or expanded to incorporate other detection means in order generate even more detailed information. For example, by varying the dynamics of the experiments (employing Molecular Recognition Force Spectroscopy) is possible to gain information relating to the affinity of binding, rate constants, and even the bond width of the binding pocket of the immobilized binding moiety. (See Hinterdorfer et al., Proc. Natl. Acad. Sci. USA, 93 1996 3477; Hinterdorfer et al., Naobiology, 4 1998 39; Ros et al., Proc. Natl. Acad. Sci. USA, 95 1998 7402; Schwesinger et al., Proc. Natl. Acad. Sci. USA, 97 2000 9972.) Similarly, by employing lateral force mapping, it is possible to gather information relating to binding as well as local topography. (See, Ludwig et al., Biophys. J. 72 1997 445; Willemsen et al., Biophys. J., 57 1998 2220.)

Accordingly, preferred embodiments of the instant invention are incorporated into any number of general or specifically tailored AFM applications. For example, in a preferred embodiment, the biosensor of the instant invention can be an AFM detection system wherein the dendritic tether is attached to an AFM tip as the substrate. In such an embodiment, the binding moiety attached to the dendritic tether is then brought in sufficient proximity to a surface containing the target analyte to allow for binding to occur. Similarly, lateral force mapping could be employed using the dendritic tethers and binding moieties of the instant invention.

Another analytical tool useful in investigating binding interactions on surfaces is surface plasmon resonance. (See Lahiri et al., Analytical Chemistry, 71(4) 1999 777–790.) SPR is particularly useful in that it allows detection of interactions in real-time. In general, SPR is carried out by measuring changes in the refractive index of a medium in close proximity to a thin film deposited on a substrate. Specifically, the resonance angle ($1_m$), which corresponds to the angle of minimum intensity of reflected light, can be altered by changes in the refractive index of the medium. (See, Raether, H., Physics of Thin Films, Hass et al., Eds. 1977 145–261; Stenberg et al., J. Colloid Interface Sci., 143 1991 513–526.) These changes in refractive index are initiated by alterations to the local environment, e.g. by anti-ligands binding to ligands attached to the surface of the film. Films useful in SPR can be comprised of binding moieties coupled to SAM forming organic molecules. In addition, organic compounds containing thiol groups are particularly preferred in order to simplify attachement of the film to a substrate.

In a preferred embodiment the instant invention is incorporated into a SPR detection system. For example, the dendritic tethers of the instant invention, with coupled binding moieties, are employed as the SAM forming species to create a thin film on a substrate. Target samples may then be passed over the substrate and alterations to the resonance angle, due to target analyte binding, can be detected.

A third analytical tool useful in measuring specific ligand/anti-ligand interactions is the quartz crystal microbalance. (See, Otto et al., J. Bacteriology, 181(17) 1999 5210–5218; Pignataro et al, Biophysical J., 78 2000 487–498.) QCM functions via applying an alternating electric field to a quartz crystal. The alternating field causes a deformation in the quartz crystal at its resonant frequency, and this frequency will lower upon increased mass load on the crystal. Accordingly, a SAM coupled to binding moieties may be formed on the crystal producing a baseline resonant frequency. Upon ligand binding to the binding moieties there would be an increase in mass load leading to a detectable change in resonant frequency.

In a preferred embodiment the instant invention is incorporated into a QCM detection system. For example, the dendritic tethers of the instant invention, with coupled binding moieties, are employed as the SAM forming species to create a thin film on the quartz crystal substrate. Target samples may then be passed over the substrate and alterations to the resonant frequencey, due to target analyte binding and increased mass load, can be detected.

EXAMPLES

The following is an example of the technology as applied for the detection of *Bacillus anthracis*. As described above, the approach to pathogen detection of the instant application could indeed be regarded as universal by coupling of appropriate binding moieties to dendrimer SAMs.

In this example, the binding moiety to be coupled to the dendritic tethers of the instant invention is an antibody against a recombinant antibody against anthrax protective antigen (PA), a necessary component of anthrax toxin, based on a monoclonal antibody originally developed by Dr. S. Leppla (NIAID, NIH). A DNA plasmid containing the gene for this binding moiety was obtained from Prof. Georgiou (Univ. Texas—Austin). The recombinant antibody consists of a pair of variable regions that specifically recognize PA with high affinity, tied together by a repeating peptide (GlyGlyGlyGlySer)$_3$. Standard methods of gene expression allow the production of large quantities of recombinant antibody protein.

While recombinant antibodies offer the advantage of high specificity, ease of modification, mass production, and small, compact size, the reduced size presents a problem for the usual methods of coupling proteins through the aspartate, glutamate or lysine residues located in various positions within the molecule. In particular, there is a high probability of compromising the antigen-binding site that represents the bulk of the recombinant antibody molecule. Even if coupling occured while the binding site was blocked, the reaction would skew the orientation of the small recombinant protein and stress the conformation of the binding site, thereby reducing its binding efficiency.

Addition of a sugar to the linker peptide, on the other hand, provides a useful functionality (aldehyde by oxidation of the attached sugar) without in any way altering the protein itself. To accomplish glycosylation in physiological conditions, so as not to denature the protein, an enzyme to transfer a sugar (N-acetylglucosamine) to one or more of the serine residues within the linker peptide was engineered. Oxidative cleavage of the sugar by $NaIO_4$ yields an aldehyde-functionalized, active recombinant antibody and provides a clean functional group ideally suited for simple coupling to a hydrazide-functionalized dendrimer tether. Periodate oxidation of a naturally glycosylated polyclonal antibody has been shown to conserve all of the antibody's ability to recognize its target antigen. This process is illustrated in Scheme 2. The dendrimer-recombinant antibody construct can then be attached to a variety of surface types to produce an active SAM for detection of pathogenic agents.

The recombinant antibody used for anthrax detection (an scFv, molecular weight 27,000 Da and a larger, better expressed variant) consist of a pair of variable regions comprising the binding site that recognizes the anthrax PA subunit. These domains are linked by a small peptide consisting of glycine and serine residues. As there is no sugar on this molecule, and attempts to use residues in the variable region would compromise its ability to recognize target antigen, glycosylation of the serine residues in the linker is accomplished using a promiscuous recombinant O-linked glycosyl transferase enzyme (POGT).

In order to produce the POGT, the native OGT enzyme gene and its translation product were characterized. The native OTG gene was initially inserted into a pET32b vector containing an embedded S-Tag sequence (received from Dr. J. Hanover (NIH)), and was subsequently inserted into *E. coli* NovaBlue and the entire gene was DNA-sequenced according to standard molecular biology techniques. The plasmid construct was then inserted into a bacterial expression host, *E. coli* BL21 (DE3), and protein expression induced by the lactose analog isopropylthio-β-D-galactoside (IPTG). Recombinant OGT protein was isolated on an S-Tag affinity column, and the enzyme purified on an S-Tag affinity column. Enzymatic activity of the native OGT was assayed with N-acetylglucosamine and casein, a protein containing the native enzyme's target sequence. N-Acetylglucosamine contains adjacent hydroxyls (C3 and C4) so it is susceptible to periodate oxidation, yielding an aldehyde, which is assayed using Purpald (Aldrich) in a standard calorimetric assay. In addition, glycosylation of peptides or proteins can be confirmed by MALDI (Matrix Assisted Laser Desorption Ionization) mass spectroscopy. The presence of an unnatural aldehyde on a peptide or protein is taken as demonstration that glycosylation has been successful, since there are no natural aldehyde functional groups in an unglycosylated protein, and it is difficult to obtain an aldehyde from an amino acid residue in aqueous solution.

In order to remove the high substrate specificity associated with OGT, the nucleotides encoding the specificity domain were excised from the gene encoding the enzyme. The modified protein was then sequenced to verify the modification, expressed, isolated and purified. Excision of a portion of the native binding domain renders the enzyme sufficiently promiscuous to glycosylate hydroxyl group residues in a wider variety of amino acid sequences. Glycosylation of the anti-PA recombinant antibody protein is demonstrated by the calorimetric assay and by MALDI. To prevent glycosylation of the antibody's active site, it is reacted with PA immobilized on an affinity resin. Once glycosylation has been accomplished, the glycosylated recombinant antibody is separated from immobilized antigen in a high-salt buffer and the antibody separated from immobilized antigen and enzyme by filtration. Subsequent oxidation of the sugar(s) is followed by attachment to a hydrazide-derivatized dendritic tether. Attachment is accomplished by allowing the aldehyde-derivatized antibody to react with the hydrazide-derivatized tether for six hours at room temperature in solution or, more conveniently, by recycling the prepared antibody in situ over a previously prepared dendritic SAM.

We claim:

1. A composition comprising:

a) a linker comprising:

i) at least a first hydrophilic polymer portion; and ii) a rigidity component portion;

b) a terminal dendrimer comprising an aryl group with at least two attachment moieties wherein said terminal dendrimer is attached to a first region of said linker; and c) a functional moiety attached to a second region of said linker.

2. A composition according to claim 1 wherein said linker further comprises a second hydrophilic polymer portion.

3. A composition according to claim 1 or 2 wherein at least one of said hydrophilic polymer portions comprises a polyethylene glycol polymer.

4. A composition according to claim 3 wherein said linker comprises two polyethylene glycol polymer portions separated by said rigidity component portion.

5. A method comprising:

a) providing a composition according to claim 1; and b) attaching a binding moiety to said functional moiety to form a binding composition.

6. A method according to claim 5 wherein said binding moiety is a polypeptide.

7. A method according to claim 5 wherein said binding moiety is an antibody or an antibody fragment.

8. A method according to claim 7 wherein said antibody or antibody fragment is recombinant.

9. A method according to claim 8 wherein said recombinant antibody or recombinant antibody fragment is glycosylated.

10. A method of attaching a first compound to a second compound by:

a) glycosylation of said first compound with a promiscuous O-linked-glycosyltransferase;

b) oxidation of said glycosylation to produce an aldehyde-derivitized first compound;

c) providing a hydrazide-derivatized second compound; and d) reacting said aldehyde-derivatized first compound with said hydrazide-derivatize second compound to attach said first compound to said second compound.

11. The method of claim 10 wherein said first compound comprises a binding moiety to a cognate.

12. The method of claim 11 wherein said glycosylation does not decrease the binding of the binding moiety to said cognate.

13. The method of claim 11 or 12 wherein said cognate is a target analyte.

* * * * *